(12) United States Patent
Tumpold

(10) Patent No.: US 11,237,098 B2
(45) Date of Patent: Feb. 1, 2022

(54) MEMS GAS SENSOR

(71) Applicant: Infineon Technologies AG, Neubiberg (DE)

(72) Inventor: David Tumpold, Kirchheim b München (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 129 days.

(21) Appl. No.: 16/774,873

(22) Filed: Jan. 28, 2020

(65) Prior Publication Data
US 2020/0309678 A1 Oct. 1, 2020

(30) Foreign Application Priority Data
Mar. 26, 2019 (EP) .................................. 19165331

(51) Int. Cl.
| | | |
|---|---|---|
| *G01N 21/17* | (2006.01) | |
| *B81B 7/02* | (2006.01) | |
| *G01N 21/3504* | (2014.01) | |
| *H05B 3/14* | (2006.01) | |
| *G01N 27/12* | (2006.01) | |
| *G01N 33/00* | (2006.01) | |
| *G01N 21/01* | (2006.01) | |

(52) U.S. Cl.
CPC ........... *G01N 21/1702* (2013.01); *B81B 7/02* (2013.01); *G01N 21/3504* (2013.01); *G01N 27/124* (2013.01); *G01N 27/128* (2013.01); *H05B 3/148* (2013.01); *B81B 2201/0214* (2013.01); *B81B 2201/0292* (2013.01); *G01N 33/0032* (2013.01); *G01N 2021/0112* (2013.01); *G01N 2021/1704* (2013.01); *G01N 2223/508* (2013.01)

(58) Field of Classification Search
CPC ............. G01N 21/1702; G01N 27/128; G01N 27/124; G01N 21/3504; G01N 33/0032; G01N 2021/0112; G01N 2223/508; B81B 7/02; B81B 2201/0214; B81B 2201/0292; B81B 2201/02

See application file for complete search history.

(56) References Cited

U.S. PATENT DOCUMENTS

2002/0142478 A1* 10/2002 Wado ................... G01N 27/124
436/151
2010/0170888 A1 7/2010 Lee et al.
2011/0296900 A1 12/2011 Thorson
(Continued)

FOREIGN PATENT DOCUMENTS

| CN | 105891271 A | 8/2016 |
|---|---|---|
| DE | 3019387 A1 | 11/1981 |
| DE | 102010003966 B3 | 5/2011 |

(Continued)

*Primary Examiner* — Benjamin R Schmitt
(74) *Attorney, Agent, or Firm* — Slater Matsil, LLP

(57) ABSTRACT

A MEMS gas sensor includes a photoacoustic sensor including a thermal emitter and an acoustic transducer, the thermal emitter and the acoustic transducer being inside a mutual measurement cavity. The thermal emitter includes a semiconductor substrate and a heating structure supported by the semiconductor substrate. The heating structure includes a heating element. The MEMS gas sensor further includes a chemical sensor thermally coupled to the heating element, and the chemical sensor including a gas adsorbing layer.

27 Claims, 10 Drawing Sheets

(56) References Cited

U.S. PATENT DOCUMENTS

2015/0021716 A1\* 1/2015 Lee ...................... G01N 27/128
257/414
2016/0237816 A1\* 8/2016 Perkins .................. G01N 21/27

FOREIGN PATENT DOCUMENTS

DE 102017205982 A1 10/2018
WO 02080620 A1 10/2002

\* cited by examiner

MEMS GAS SENSOR

This application claims the benefit of European Patent Application No. 19165331.0, filed on Mar. 26, 2019, which application is hereby incorporated herein by reference.

TECHNICAL FIELD

Embodiments of the present disclosure relate to a MEMS (Micro Electro Mechanical System) gas sensor, for example a gas sensitive infrared source for physically sensing gases combined with a chemical gas sensor.

BACKGROUND

The sensing of environmental parameters, such as noise, sound, temperature and gases gains more and more importance within mobile devices, home automation and the auto-motive sector. Harmful gas concentrations can occur due to pollution and malfunction of certain devices. The well-being is strongly influenced by the air quality. Gas detection by cheap, always available and connected sensors is an upcoming topic in the future.

There are several types of heater concepts existing. Three exemplary conventional infrared sources are LED, LASER or structures where a power loss leads to high temperatures, wherein the latter currently dominates the market. Physical gas sensors mostly need an IR source which is emitting IR wavelength, wherein most of the common devices are resistive structures which are heated up to be used as black-body or gray-body applications. Chemical gas sensors instead frequently use functionalized layers to adsorb gas molecules and change the resistor value of these layers to sense the gas, wherein these structures need to be heated up again to "free" the molecules hence to refresh/reset the sensing structure. However, common chemical gas sensors are not able to detect $CO_2$ or to calculate the equivalent $CO_2$ value ($eCO_2$) out of VOCs (Volatile Organic Compounds). Therefore, if different kinds of gases should be measured, it often happens that a physical gas sensor and a separate chemical gas sensor are required for this task.

DE 10 2010 003 966 B3 describes a sensor arrangement including an optical gas sensor and a chemical gas sensor. A ceramic carrier including a resistive heater is provided, wherein a metal oxide layer of a chemical sensor is arranged at one side of the ceramic carrier and wherein a layer for coupling out infrared radiation is arranged at the opposite side of the ceramic carrier. Upon energizing the resistive heater, the ceramic carrier heats up and emits infrared radiation, wherein the ceramic carrier heats up conformally so that the whole ceramic carrier comprises a uniform temperature over its entire body. However, the physical gas sensor may work at a different temperature than the chemical gas sensor. Therefore, due to the uniform temperature distribution over the entire ceramic carrier, gas sensing may work sufficiently for one of the chemical and the physical gas sensor but not for the other.

Thus, it is desired to improve existing solutions for sensing one or more gases.

SUMMARY

Accordingly, the present disclosure describes a possible infrared MEMS heater which is able to sense simultaneously various environmental gases. The system as disclosed herein can be used to combine physical gas sensors and chemical gas sensors at the same time on the same MEMS device.

A first aspect of the present disclosure concerns a MEMS gas sensor comprising, inter alia, a photoacoustic sensor comprising a thermal emitter and an acoustic transducer, both being arranged in a mutual measurement cavity. The photoacoustic sensor may be configured to detect a gas in an environment according to the photoacoustic principle. Accordingly, the thermal emitter may be configured to emit thermal radiation, e.g. infrared radiation, in a predetermined wavelength spectrum into the measurement cavity. The particular wavelength of the emitted thermal radiation may depend on the gas to be detected, i.e. the so-called analyte or target gas. The emitter may be configured to intermittently emit the thermal radiation. Accordingly, the environmental gas inside the measurement cavity, including the target gas, absorbs the intermittently emitted thermal radiation and, in consequence, the gases intermittently heats up and cools down in reaction to the intermittently emitted thermal radiation. This intermittent absorption and related heating and cooling of the gases inside the measurement cavity may produce an alternating increase and decrease of pressure inside the measurement cavity. These pressure variations may be detected by the acoustic transducer, for example a MEMS microphone. The amount of absorption of the emitted thermal radiation by the gases and the related pressure variations inside the measurement cavity may depend on the sort of gas inside the cavity and it may vary with the respective target gas. Each target gas may comprise a characteristic absorption spectrum, i.e. it may cause characteristic pressure variations in response to the intermittently emitted thermal radiation. Said characteristic absorption spectrum may also be referred to as a gas-specific fingerprint. Accordingly, the acoustic transducer may record a signal that may be characteristic for the respective target gas, such that the acoustic transducer may thereby detect and identify the respective target gas. The thermal emitter for emitting the thermal radiation may comprise a semiconductor substrate and a heating structure being supported by the semiconductor substrate, wherein the heating structure comprises a heating element. The heating element may, for instance, be supported by the heating structure, be embedded in the heating structure, be attached to the heating structure, be mounted in, at or on the heating structure, be fixed to the heating structure, or be otherwise coupled with the heating structure. The MEMS gas sensor further comprises a chemical gas sensor being thermally coupled to the heating element, the chemical gas sensor including a gas adsorbing layer. Therefore, heat that is produced by the thermal emitter may also reach the chemical gas sensor and may heat up the gas sensor, and in particular the gas adsorbing layer. Accordingly, the thermal emitter of the MEMS gas sensor may be a dual-use thermal emitter since it may be used both for physically detecting a target gas by the photoacoustic principle and for chemically detecting a target gas by a chemical sensing principle. The chemical sensing principle may be based on adsorption of molecules of the respective target gas by the gas adsorbing layer, i.e. the gas adsorbing layer may be configured to adsorb molecules of a respective target gas. A MEMS gas sensor comprising said heating element comprised by the heating structure and being supported by a semiconductor substrate is a different type of gas sensor as compared to gas sensors comprising ceramic bodies. The heating structure may be heated by energizing the heating element. Since the heating structure is supported by the semiconductor substrate, temperature distribution may vary between the heating structure and the semiconductor substrate. The heating structure and the semiconductor substrate may heat up non-conformally or unevenly such that different temperature regions may result in different areas of the MEMS gas sensor. For example, physical gas sensor elements may be arranged at a temperature region that may be particularly suitable for physical gas sensing while chemical gas sensor elements, such as the gas adsorbing layer, may be arranged at a temperature region that may be particularly suitable for chemical gas sensing.

A second aspect of the present disclosure concerns a thermal emitter comprising, inter alia, a semiconductor substrate and a heating structure being supported by the semiconductor substrate. The heating structure may comprise a heating element. The thermal emitter may further comprise a chemical sensor thermally coupled to the heating element, the chemical sensor including a gas adsorbing layer. The thermal emitter of the second aspect may be combined with and/or used in the MEMS gas sensor of the first aspect. Accordingly, each and every feature of the first aspect may be combined with the thermal emitter of the second aspect. In particular, each claim of the first aspect may be combined with the thermal emitter of the second aspect, which combinations are originally disclosed herewith.

BRIEF DESCRIPTION OF THE DRAWINGS

In the following, embodiments of the present disclosure are described in more detail with reference to the figures, in which.

DETAILED DESCRIPTION OF ILLUSTRATIVE EMBODIMENTS

Figure 1A:
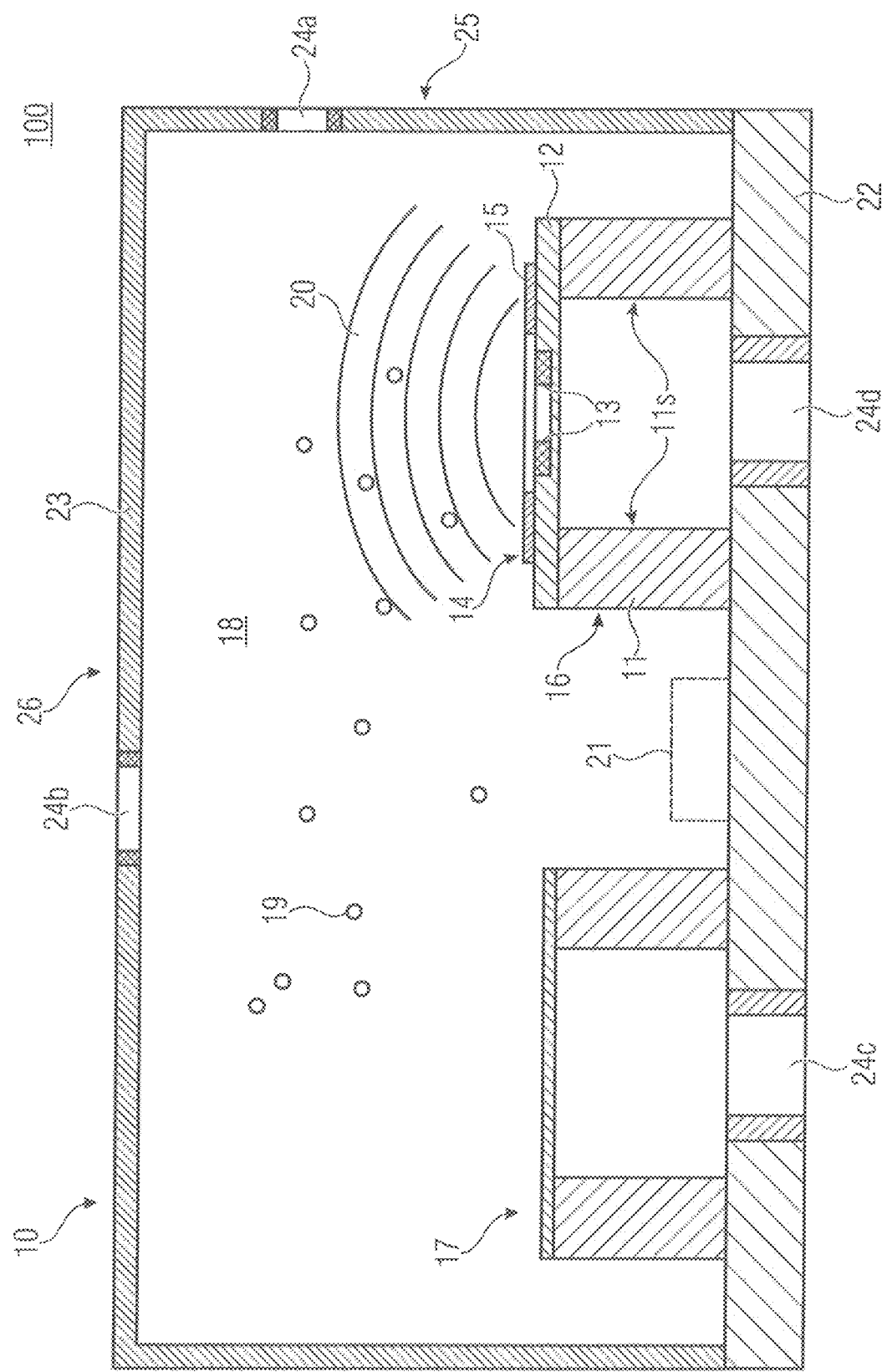
FIG. 1A shows a schematic cross-sectional view of a MEMS gas sensor according to an embodiment.

Equal or equivalent elements or elements with equal or equivalent functionality are denoted in the following description by equal or equivalent reference numerals.

Method steps which are depicted by a block diagram and which are described with reference to said block diagram may also be executed in an order different from the depicted and/or described order. Furthermore, method steps concerning a particular feature of a device may be replaceable with said feature of said device, and the other way around.

In the following description, infrared radiation is mentioned as one non-limiting example of a thermal radiation. Thermal radiation may be any radiation above absolute zero starting at 0° Kelvin. Infrared radiation may be a particular part of a thermal radiation in general.

Furthermore, a membrane will be mentioned in the following as a non-limiting example of a heating structure. A membrane may comprise a width or a height that is substantially smaller than its dimensions in the lateral extension direction. However, the heating structure according to the herein described concept may not be limited to a membrane only.

Thicknesses of certain elements, for example thicknesses of the membrane structure, the semiconductor substrate, the heating structure, the heating element and the gas adsorbing layer may not be drawn to scale.

FIG. 1A shows a MEMS gas sensor 100 according to a first exemplary embodiment. The MEMS gas sensor 100 may comprise a photoacoustic sensor 10. The photoacoustic sensor 10 may comprise a thermal emitter 16 and an acoustic transducer 17. Both the thermal emitter 16 and the acoustic transducer 17 are arranged inside a mutual measurement cavity 18. The photoacoustic sensor 10 may comprise said measurement cavity 18. The measurement cavity 18 may be a substantially closed cavity surrounding the thermal emitter 16 and the photoacoustic transducer 17, wherein the measurement cavity 18 may comprise at least one opening through which environmental gases, e.g. ambient air, may flow into the measurement cavity 18. The gas inside the measurement cavity 18 is symbolized by a plurality of schematic gas molecules 19. At least one target gas inside the measurement cavity 18 may be detected and/or identified by the photoacoustic sensor 10 according to the physical photoacoustic principle.

The thermal emitter 16 may comprise a semiconductor substrate 11 and a heating structure 12 being supported by the semiconductor substrate 11. Said heating structure 12 may, for instance, include a membrane structure or be a membrane structure, e.g. a membrane or a diaphragm. In this document, the terms heating structure, membrane and membrane structure may therefore be used synonymously.

The heating structure 12, which may also be referred to as a diaphragm structure, may comprise at least one heating element 13 that may be supported by the heating structure 12. As a non-limiting example, the heating element 13 may be embedded in the heating structure 12. The heating element 13 may comprise a loop-shape, for example, such as exemplarily shown in FIG. 1A. Of course, the loop-shape may only be one of several non-limiting examples of possible geometrical forms. A more detailed explanation of the heating element 13 will follow further below with reference to FIGS. 4A and 4B.

The thermal emitter 16 may be configured to emit heat or thermal radiation 20, e.g. infrared radiation, in an operating temperature range of the photoacoustic sensor 10, for example a first temperature range for operating the photoacoustic sensor 10 for physically (i.e. according to a physical principle, e.g. the photoacoustic principle) detecting at least a first target gas inside the measurement cavity 18. For example, the emitter 16 may be configured to intermittently emit the heat or thermal radiation 20. The emitted heat or thermal radiation 20 may be absorbed, at least partially, by the gas molecules 19 which heat up accordingly. If the heat or thermal radiation 20 is no longer emitted by the thermal emitter 16, no heat or thermal radiation can be absorbed anymore by the gas molecules 19 and they cool down again. This intermittent heating and cooling induces a pressure variation inside the measurement cavity 18.

This pressure variation may be detected by the acoustic transducer 17 which may transduce the measured pressure variation into a corresponding measurement signal. The acoustic transducer 17 may, for instance, comprise a microphone, e.g. a MEMS micro-phone.

The photoacoustic sensor 10 may further comprise a controller 21, for example an integrated circuit, e.g. an ASIC (Application Specific Integrated Circuit). The controller 21 may be arranged inside or outside the measurement cavity 18. Thus, it is depicted in dashed lines in FIG. 1A. The controller 21 may receive the measurement signal from the acoustic transducer 17 and it may process the measurement signal so as to identify the at least one target gas according to the photoacoustic principle.

In addition to the physical photoacoustic sensor 10, the MEMS gas sensor 100 may further comprise a chemical sensor 14 for chemically detecting a target gas, which may be the above mentioned at least one target gas or a different second target gas. The chemical gas sensor 14 may be coupled to the above described controller 21 for processing a measurement signal received from the chemical sensor 14 so as to identify the target gas according to a chemical principle. Alternatively, the chemical sensor 14 may comprise its own dedicated controller, i.e. the chemical sensor 14 may be coupled to a controller separate from the controller 21 being coupled with the photoacoustic sensor 10.

The chemical sensor 14 may comprise a gas adsorbing layer 15. The gas adsorbing layer 15 may provide the functionality of adsorbing molecules 19 of a gas to be sensed (analyte or target gas) inside the measurement cavity 18. Thus, the gas adsorbing layer 15 may also be referred to as a functionalized layer. According to some examples, the gas adsorbing layer 15 may include graphene and/or metal oxide (MOX).

The gas adsorbing layer 15 may adsorb one or more of the gas molecules 19 inside the measurement cavity 18. The gas adsorbing layer 15 may comprise a predetermined operating temperature at which adsorption of gas molecules 19 is better than compared to other non-operating temperatures. The gas adsorbing layer 15 may become saturated over time with increased adsorption of gas molecules 19. In order to refresh the gas adsorbing layer 15, the gas adsorbing layer 15 may be heated up to a predetermined refreshing temperature at which the gas adsorbing layer 15 may be enabled to desorb the adsorbed gas molecules 19 in order to relieve the gas molecules 19 again.

Furthermore, the MEMS gas sensor 100 may comprise a substrate 22, for instance a PCB (Printed Circuit Board). A lid 23 may be arranged on said substrate 22 for covering the thermal emitter 16 and/or the acoustic transducer 17 and for providing the measurement cavity 18. The lid 23 may provide a housing for the thermal emitter 16 and the acoustic transducer 17. The lid 23 may comprise one or more openings 24a, 24b for providing a fluid communication with the surrounding, for example for allowing environmental gases and/or at least one target gas to enter the measurement cavity 18. For example, one or more openings 24a may be arranged in the lateral side walls 25 of the lid 23. Additionally or alternatively, one or more openings 24b may be arranged in the top wall 26 (i.e., the wall opposite the substrate 22) of the lid 23.

Additionally or alternatively, one or more openings 24c, 24d may be arranged in the substrate 22. For example an opening 24c may be arranged underneath the acoustic transducer 17. Additionally or alternatively, an opening 24d may be arranged underneath the thermal emitter 16.

The thermal emitter 16 may comprise the semiconductor substrate 11. The semiconductor substrate 11 may comprise the heating structure 12. The semiconductor substrate 11 may support the heating structure 12, wherein the heating structure 12 may be arranged at laterally surrounding side walls 11s of the semiconductor substrate 11 and/or on top of said laterally surrounding side walls 11s of the semiconductor substrate 11.

The heating structure 12 may comprise the heating element 13. In this non-limiting example as shown in FIG. 1A, the heating element 13 may be, at least partially, embedded in the heating structure 12, e.g. membrane. The heating element 13 may, for instance, be supported by the heating structure 12 in a different way, for example by being arranged on a first or second surface of the heating structure 12. For example, the heating element 13 may be arranged on a surface facing the substrate 22, i.e. on a surface at the bottom side of the heating structure 12. Additionally or alternatively, the heating element 13 may be arranged on the opposite surface, i.e. on a surface at the top side of the heating structure 12. The heating element 13 may, however, also be arranged on both a first and a second surface (e.g., top and bottom side) of the heating structure 12.

The embodiment shown in FIG. 1A may comprise the above discussed gas adsorbing layer 15. The gas adsorbing layer 15 may comprise different geometrical shapes, for example an annular or loop shape, or a continuous shape without any geometrical interruptions. The gas adsorbing layer 15 may be supported by the thermal heater 16, and in particular by at least one of the heating structure 12 and the semiconductor substrate 11.

Figure 1B:
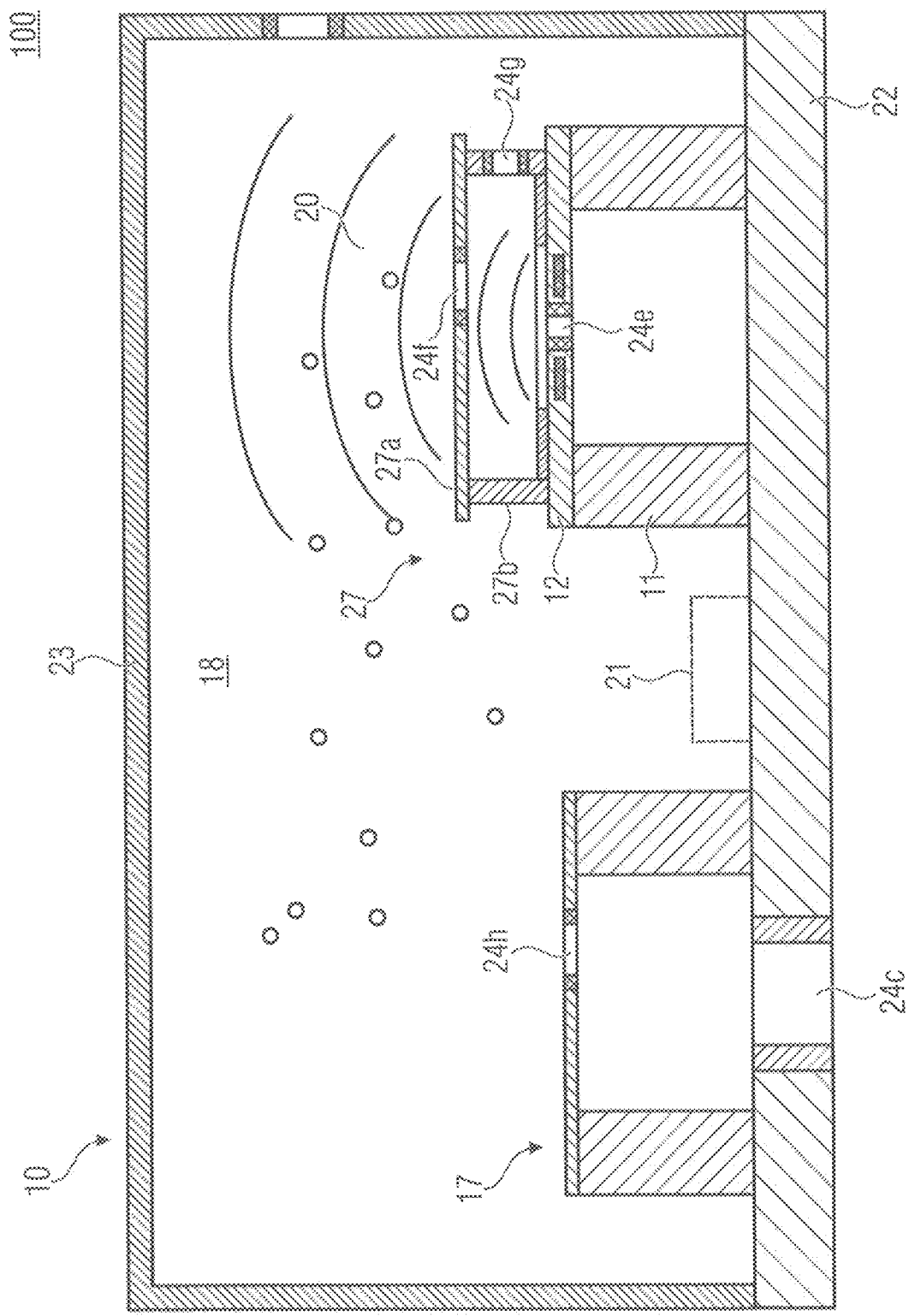
FIG. 1B shows a schematic cross-sectional view of a MEMS gas sensor according to an embodiment.

FIG. 1B shows a further example of a MEMS gas sensor 100 according to the herein described concept. The features of the embodiment of FIG. 1B may be combined with the features of the embodiment of FIG. 1A and vice versa. Thus, only differences to the previously discussed embodiments shall be described in the following.

As shown in FIG. 1B, the thermal emitter 16 may comprise a filter structure 27. The filter structure 27 may comprise a window or a filter element 27a and a supporting structure 27b for supporting the filter element 27a. The filter structure 27 may be configured to selectively transmit only thermal radiation at a predetermined wavelength spectrum, for example only infrared radiation at a particular infrared wavelength spectrum.

The filter structure 27 may be supported by the thermal emitter 16, and more particularly by the semiconductor substrate 11 and/or the heating structure 12. The filter structure 27 may, in a projection perpendicular to the heating structure 12, laterally surround the heating element 13.

Additionally or alternatively to the above discussed one or more openings 24a, 24b, 24c, 24d one or more further openings 24e, 24f, 24g, 24h may be provided for allowing a gas flow. For example, the heating structure 12 may comprise one or more openings 24e for allowing a flow of gas between the measurement cavity 18 and an inside portion of the thermal emitter 16. Additionally or alternatively, though not explicitly shown, the heating element 13 may comprise one or more openings. Additionally or alternatively, the filter structure 27 may comprise one or more openings 24f, 24g. In particular, at least one of the filter element 27a and the supporting structure 27b may comprise one or more openings 24f, 24g. Additionally or alternatively, the acoustic transducer 17 may comprise one or more openings 24h.

As can be seen in both of the above discussed FIGS. 1A and 1B, and according to the herein described principle, the chemical sensor 14, and in particular the gas adsorbing layer 15, may be thermally coupled to the heating element 13. The heating element 13 may be configured to generate heat. The heating element 13 may heat up the heating structure 12 and, at least partially, the semiconductor substrate 11. The thermal emitter 16, and in particular the heating structure 12, may emit or dissipate heat into the environment. Heat may be dissipated by the thermal emitter 16 in a temperature range covering at least one of the above described operating temperature and refreshing-temperature of the gas adsorbing layer 15.

Accordingly, the thermal emitter 16 may be configured to emit heat or thermal radiation (e.g., infrared radiation) at a first temperature range $\Delta T_1$ for operating the photoacoustic sensor 10 for physically detecting at least a first target gas inside the measurement cavity 18, and to emit heat or thermal radiation (e.g., infrared radiation) at a second temperature range $\Delta T_2$ for operating the adsorbing layer 15 for adsorbing and/or desorbing gas molecules for chemically detecting the first and/or a second target gas inside the measurement cavity 18. In other words, the thermal emitter 16 may be configured to emit thermal radiation inside a first temperature range $\Delta T_1$ for operating the photoacoustic sensor 10, and to emit thermal radiation inside a second temperature range $\Delta T_2$ for operating the chemical sensor 14.

According to an example, the first temperature range $\Delta T_1$ may be between 400° C. and more, or between 450° C. and 900° C. Additionally or alternatively, the second temperature range $\Delta T_2$ may be between 300° C. and less, or between 350° C. and 100° C.

Therefore, the chemical sensor 14, and in particular the gas adsorbing layer 15, may be thermally coupled to the heating element 13 by being arranged at certain locations, e.g. at certain predetermined portions of the thermal emitter 16. Each thermal emitter 16 may have its own characteristic temperature profile. A temperature profile may indicate areas of high temperature, so-called hot-spots, and areas of a lower temperature.

Figure 2A:
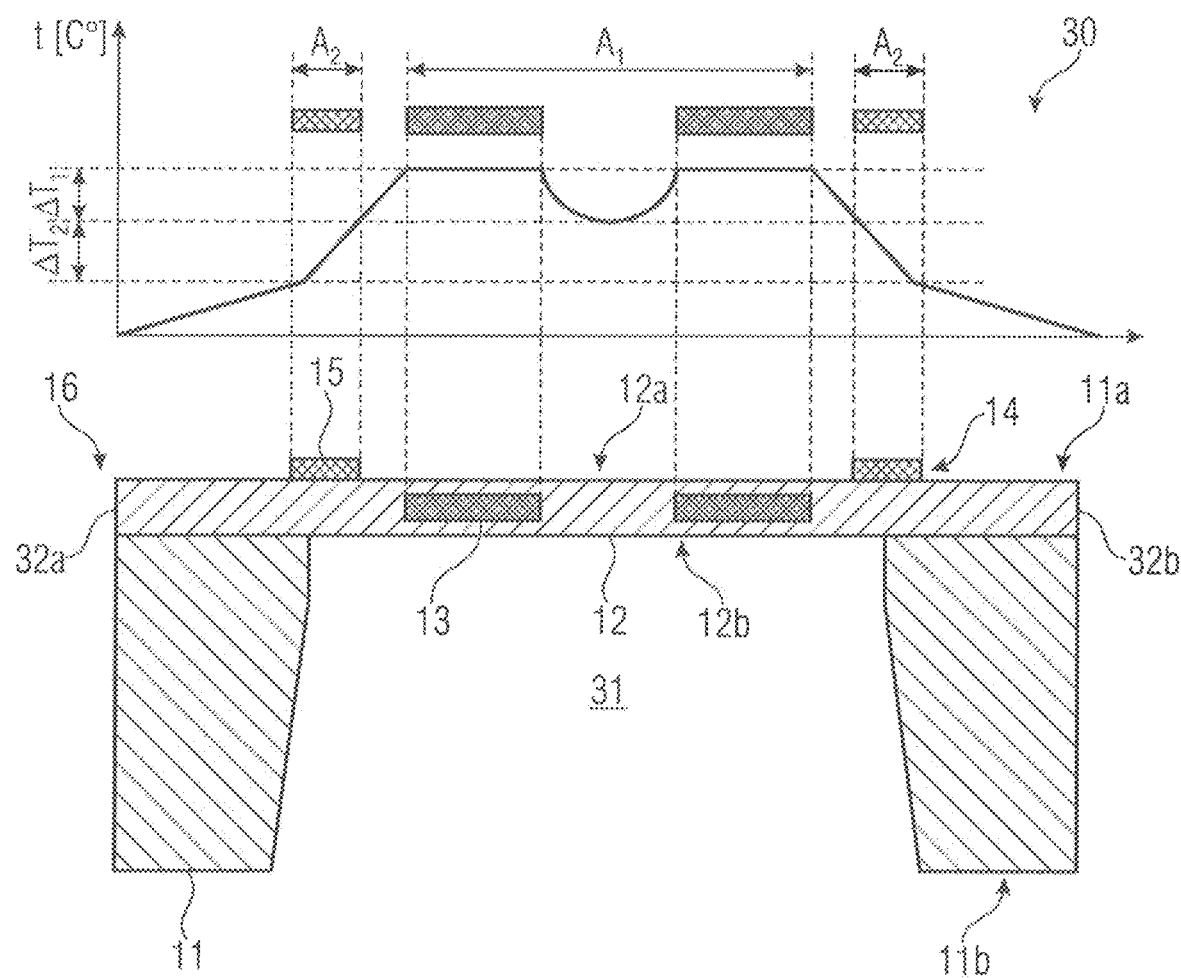
FIG. 2A shows a schematic cross-section of a thermal emitter and a corresponding temperature profile according to an embodiment.
Figure 2B:
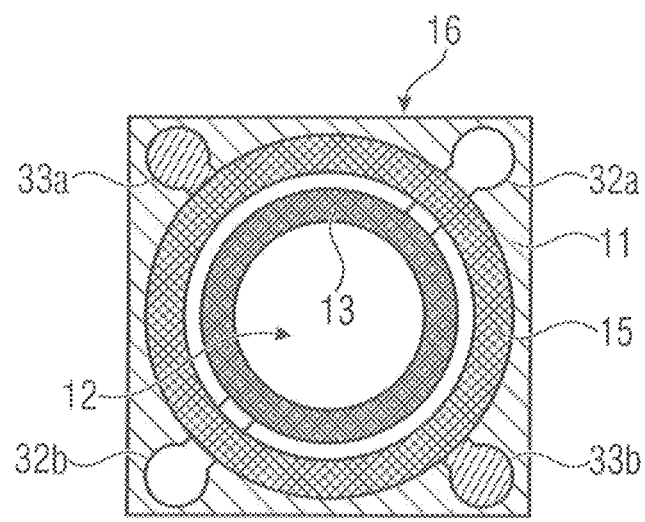
FIG. 2B shows a schematic top view of the thermal emitter of FIG. 2.

FIGS. 2A and 2B show an example of a temperature profile (FIG. 2A top) belonging to an exemplary embodiment of a thermal emitter 16 (FIG. 2A bottom). FIG. 2A bottom shows a side view of the exemplary thermal emitter 16, and FIG. 2B shows a top view of the thermal emitter 16 of FIG. 2A bottom.

The thermal emitter 16 comprises a semiconductor substrate 11 having a first side 11a (top) and an opposite second side 11b (bottom). The semiconductor substrate 11 may comprise an opening 31 extending through at least parts of or through the entire semiconductor substrate 11 between the first side 11a and the second side 11b.

A heating structure 12, e.g. a membrane, may be supported by the semiconductor substrate 11. As shown in the non-limiting example of FIG. 2A, the heating structure 12 may be arranged nearer to the first side (top) 11a of the semiconductor substrate 11 than to the second side (bottom) 11b of the semiconductor substrate 11.

The heating structure 12 may comprise a heating element 13. The heating element 13 may, for example, be embedded in the heating structure 12. A chemical gas sensor 14 comprising a gas adsorbing layer 15 may be thermally coupled with the heating structure 12 and/or the heating element 13, for example by being arranged on or at the heating structure 12. For instance, the gas adsorbing layer 15 may be disposed directly on a top or a bottom surface 12a, 12b of the heating structure 12. The top surface 12a of the heating structure 12 may be a first surface of the heating structure 12 facing towards the measurement cavity 18 when assembled (c.f. FIG. 1A), while the bottom surface 12b of the heating structure 12 may be an opposite second surface of the heating structure 12 facing away from the measurement cavity 18 when assembled.

The heating structure 12 may comprise a central portion and a peripheral portion surrounding said central portion. The heating element 13 may be arranged at said central portion. The gas adsorbing layer 15 may be arranged at said peripheral portion. In other words, the gas adsorbing layer 15 may be disposed over or under the peripheral portion of the heating structure 12, i.e. along the peripheral portion at the first (top) surface 12a or along the peripheral portion at the second (bottom) surface 12b of the heating structure 12.

The chemical gas sensor 14, and in particular the gas adsorbing layer 15, may be directly thermally coupled to the heating structure 12 by being in direct contact with at least parts of the heating structure 12. Alternatively, the chemical gas sensor 14, and in particular the gas adsorbing layer 15, may be indirectly thermally coupled to the heating structure 12, e.g. by one or more components, such as for example thermally conducting layer(s), which may be arranged between the gas adsorbing layer 15 and the heating structure 12. Accordingly, the gas adsorbing layer 15 may be either directly or indirectly (e.g. by one or more components) thermally coupled to the heating structure 12. Heat from the heating element 13 may be transferred through the heating structure 12 to the chemical gas sensor 14, and in particular to the gas adsorbing layer 15.

Optionally, electrical connectors (not explicitly shown) may be provided for electrically contacting the heating element 13 for activating same so that the heating element 13 produces heat. Additionally or alternatively, signal connectors (not explicitly shown) may be provided for receiving signals, such as measurement signals, from the chemical gas sensor 14.

At the time of activation of the heating element 13, it produces heat that may spread through the heating structure 12. This heat may be emitted or dissipated by the heating structure 12, preferably into the measurement cavity 18 in the form of thermal (e.g., infrared) radiation. Since the heating structure 12 may be supported by the semiconductor substrate 11, emitted heat may also spread over the semiconductor substrate 11. This heat spreading may be different for different types of thermal emitters 16. Accordingly, each thermal emitter 16 and each heating structure 12 may comprise an individual and predetermined temperature profile, as will be discussed in further detail below.

In FIG. 2A the predetermined temperature profile 30 belonging to the exemplary depicted thermal emitter 16 is shown above said thermal emitter 16. The depicted temperature profile 30 shows the temperature (y-axis) as a function of a distance (x-axis) from the center of the heating structure 12. Accordingly, the temperature profile 30 may indicate a heat distribution depending on a lateral distance from the heating element 13.

As can be seen, the thermal emitter 16 and/or heating structure 12, respectively, may comprise a first portion $A_1$ (e.g., an area or region) at which the temperature lies within a first temperature range $\Delta T_1$. This first portion $A_1$ may be an area at or near the heating element 13. Accordingly, the heating element 13 may be configured to heat this first portion $A_1$ of the thermal emitter 16 and/or heating structure 12, respectively, to a first temperature $T_1$ inside the first temperature range $\Delta T_1$.

The thermal emitter 16 and/or heating structure 12, respectively, may comprise a second portion $A_2$ (e.g., an area or region) at which the temperature lies within a second temperature range $\Delta T_2$. The second temperature range $\Delta T_2$ may be lower than the first temperature range $\Delta T_1$. The first and second temperature ranges $\Delta T_1$, $A_2$ may have a mutual border or they may overlap to a certain extent.

The second portion $A_2$ may be an area adjacent to and/or laterally distanced from the heating element 13. Accordingly, the heating element 13 may be configured to heat this second portion $A_2$ of the thermal emitter 16 and/or heating structure 12, respectively, to a second temperature $T_2$ inside the second temperature range $\Delta T_2$.

The first temperature $T_1$ at the first area $A_1$ may correspond to an operating temperature of the photoacoustic sensor 10. The first temperature range $\Delta T_1$ may correspond to an operating temperature range of the photoacoustic sensor 10. The first temperature $T_1$ may lie inside the first temperature range $\Delta T_1$. The second temperature $T_2$ at the second area $A_2$ may correspond to an operating temperature of the chemical sensor 14. The second temperature range $\Delta T_2$ may correspond to an operating temperature range of the chemical sensor 14. The second temperature $T_2$ may lie inside the second temperature range $\Delta T_2$. The chemical sensor 14, and in particular the gas adsorbing layer 15, may be arranged at said second area $A_2$.

Summarizing, the thermal emitter 16 and/or heating structure 12, respectively, may comprise a predetermined temperature profile 30 according to which the heating element 13 is configured to heat a first portion $A_1$ of the thermal emitter 16 and/or of the heating structure 12, respectively, to a first temperature $T_1$ and to heat a second portion $A_2$ of the thermal emitter 16 and/or of the heating structure 12, respectively, to a second temperature $T_2$, wherein the adsorbing layer 15 is arranged at the second portion $A_2$ of the thermal emitter 16 and/or heating structure 12. The second temperature $T_2$ may be lower than the first temperature $T_1$.

The heating element 13 in combination with the heating structure 12, e.g. membrane, may be configured as a thermal radiation source, e.g. an infrared radiation source. Thermal radiation produced by said thermal radiation source 12, 13 may be used for a physical gas sensing principle, e.g. in photoacoustic sensor systems or in non-dispersive infrared (NDIR) sensor systems. Different kinds of target gases may require different wavelengths to be emitted by the thermal radiation source 12, 13. As a non-limiting example, the thermal emitter 16 (e.g., by the thermal radiation source 12, 13) may be configured to emit heat at temperatures between 300° C. and 900° C. or higher, which may correspond to the above discussed operating temperature range $\Delta T_1$ of the photoacoustic sensor 10.

The chemical gas sensor 14 may comprise the above mentioned gas adsorbing layer 15 for sensing a gas according to a chemical gas sensing principle. Molecules of a target gas (analyte) may be adsorbed by the gas adsorbing layer 15. The gas adsorbing layer 15 may preferably adsorb gas molecules at a temperature inside a predetermined adsorbing temperature range $\Delta T_{2a}$. The gas adsorbing layer 15 may be saturated once a critical number of gas molecules have been adsorbed. In order to refresh, recover, reset and/or reactivate the gas adsorbing layer 15, the gas adsorbing layer 15 may be heated up to a recovery or refreshing temperature inside a desorbing temperature range $\Delta T_{2d}$ at which the adsorbed gas molecules may desorb from the adsorbing layer 15. Said desorbing temperature range may cover a range between 50° C. and 500° C., or between 100° C. and 350° C. The desorbing temperature range $\Delta T_{2d}$ may be lower than the adsorbing temperature range $\Delta T_{2a}$. At least one of the adsorbing temperature range $\Delta T_{2a}$ and the desorbing temperature range $\Delta T_{2d}$ may be covered by the above described operating temperature range $\Delta T_2$ of the chemical sensor 14.

The MEMS gas sensor 100 may be configured to sense different target gases, preferably at the same time, by combining physical and chemical gas sensing principles. That is, heat being produced by the heating element 13 may be used for both the physical and the chemical sensing principle, preferably at the same time. Accordingly, the MEMS gas sensor 100 may be configured to sense a first target gas based on a physical sensing principle by the photoacoustic sensor 10, and the MEMS gas sensor 100 may be configured to sense, preferably at the same time, the first and/or a second target gas based on a chemical sensing principle by the chemical sensor 14 comprising the gas adsorbing layer 15. Both sensing principles may rely on heat emitted by the thermal emitter 16.

Therefore, the heating element 13 may be configured to heat the above mentioned first portion $A_1$ of the thermal emitter 16 and/or heating structure 12, respectively, to the above mentioned first temperature $T_1$ and to heat the second portion $A_2$ of the thermal emitter 16 and/or heating structure 12, respectively, to the second temperature $T_2$, preferably during the same activation time. That is, during activation of the heating element 13, the MEMS gas sensor 100 may be configured to simultaneously detect a first target gas by the photoacoustic sensor 10 and to detect the first and/or a second target gas by the chemical sensor 14.

The heating element 13 may heat itself up to a predetermined temperature range, for example between 50° C. and 1200° C. or higher. The heat from the heating element 13 may spread through the thermal emitter 16, such that the thermal emitter 16 may comprise areas $A_1$ having higher temperatures and areas $A_2$ having lower temperatures. Depending on the construction of the thermal emitter 16 and/or of the heating structure 12, respectively, each thermal emitter 16 and/or heating structure 12 may comprise its own characteristic temperature profile 30 indicating its "high temperature zones" and "low temperature zones", wherein the areas $A_1$, $A_2$ of the thermal emitter 16 and/or of the heating structure 12 in which the heating element 13 may be arranged, could be located in different temperature zones, as will be discussed in more detail somewhat later with reference to FIG. 2C.

However first, as can be seen in FIGS. 2A and 2B the gas adsorbing layer 15 may be arranged, at least partially, at the heating structure 12 and/or at least partially at the semiconductor substrate 11. Alternatively, the gas adsorbing layer 15 may be arranged entirely at the heating structure 12 only and/or entirely at the semiconductor substrate 11 only.

In more general terms, the position of the gas adsorbing layer 15 may depend on the characteristic temperature profile 30 of the thermal emitter 16 and/or of the heating structure 12, respectively, as exemplarily depicted in the graph in FIG. 2A top. For example, the gas adsorbing layer 15 may be disposed at the second region $A_2$ of the thermal emitter 16 and/or the heating structure 12, which is a "low temperature zone" comprising a temperature inside the above described operating temperature range $\Delta T_2$ of the chemical sensor 14, which may include the adsorbing temperature range $\Delta T_{2a}$ and/or the desorbing temperature range $\Delta T_{2d}$.

According to the non-limiting example shown in FIGS. 2A and 2B, the thermal emitter 16 and/or the heating structure 12, respectively, may comprise a characteristic temperature profile 30 according to which temperature decreases with increasing lateral distance from the center, or with increasing lateral distance from the heating element 13.

A non-limiting example of the above mentioned temperature zones of the thermal emitter 16 and/or the heating structure 12, and in particular an example of the above mentioned "low temperature zones" and "high temperature zones", will now be discussed in more detail with reference to FIG. 2C.

Figure 2C:
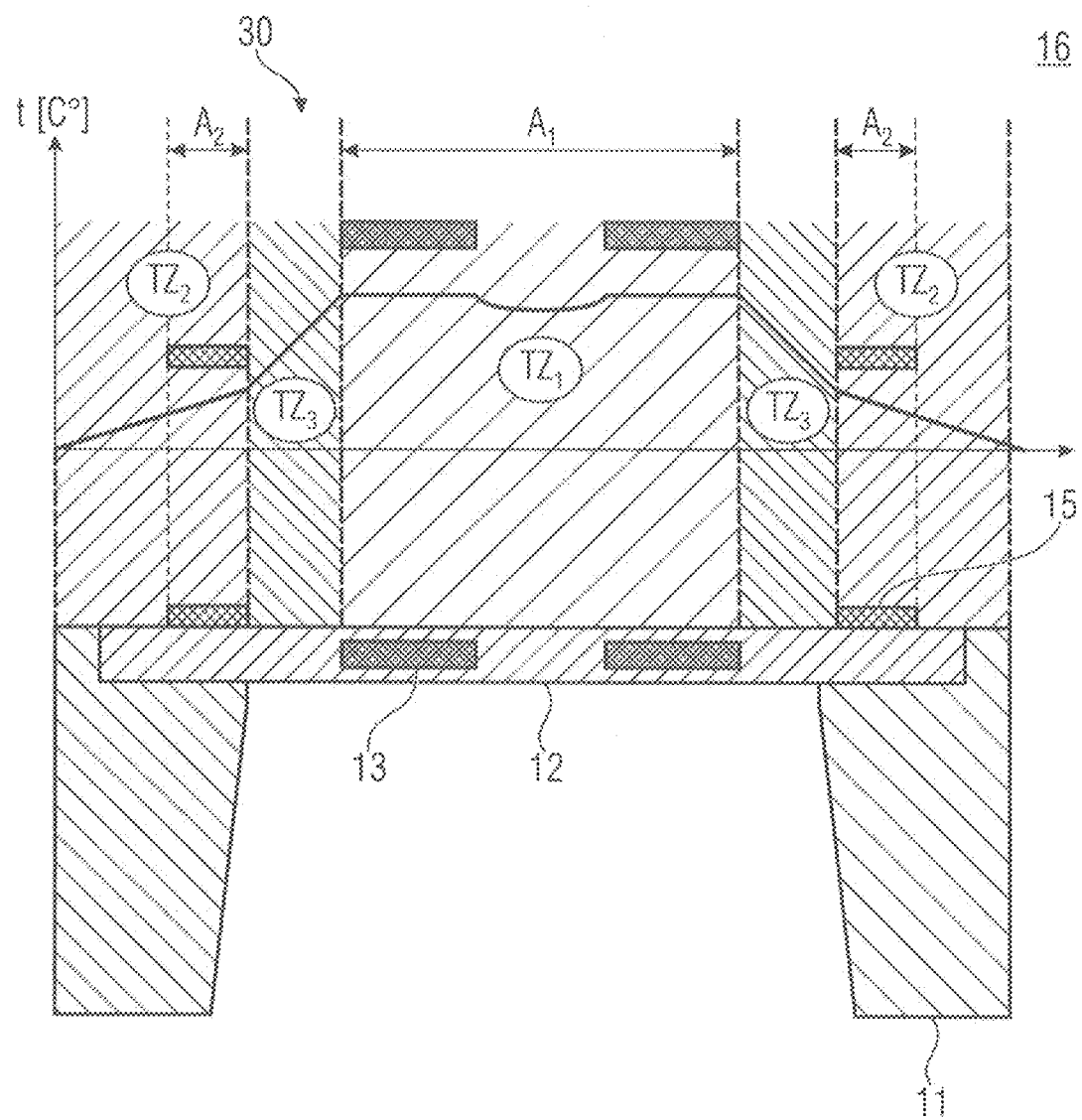
FIG. 2C shows a schematic cross-section of a thermal emitter and a corresponding temperature profile with different temperature zones according to an embodiment.

As can be seen in FIG. 2C, the thermal emitter 16 and/or the heating structure 12 may comprise a predetermined temperature profile 30 according to which the thermal emitter 16 and/or the heating structure 12, respectively, comprise at least three different temperature zones $TZ_1$, $TZ_2$, $TZ_3$. A first temperature zone $TZ_1$ may be located at or near the heating element 13. A second temperature zone $TZ_2$ may be arranged adjacent to and laterally spaced from the heating element 13. A third temperature zone $TZ_3$ may be located between the first and second temperature zones $TZ_1$ and $TZ_2$.

As can be seen by the slope of the graph representing the respective temperature zone $TZ_1$, $TZ_2$, $TZ_3$ in the temperature profile 30, temperature variations in the first and second temperature zones $TZ_1$, $TZ_2$, may be less than temperature variations in the third temperature zone $TZ_3$. In other words, temperature in the first temperature zone $TZ_1$ may remain almost constant, i.e. the slope of the graph in the first temperature zone $TZ_1$ is low or almost zero. Temperature in the second temperature zone $TZ_2$ may vary, e.g. by slightly decreasing. Accordingly, the slope of the graph in the second temperature zone $TZ_2$ is slightly falling towards the peripheral portions of the thermal emitter 16 and/or the heating structure 12, respectively. Temperature in the third temperature zone $TZ_3$ may vary more than in the second temperature zone $TZ_2$ and/or than in the first temperature zone $TZ_1$. This can be seen in the non-limiting example of FIG. 2C since the temperature in the third temperature zone $TZ_3$ rapidly drops, i.e. the slope of the graph in the third temperature zone $TZ_3$ is steeper than in the second temperature zone $TZ_2$ and/or than in the first temperature zone $TZ_1$.

The first temperature zone $TZ_1$ may comprise a higher mean or average temperature than the second and third temperature zones $TZ_2$, $TZ_3$. The first temperature zone $TZ_1$ may therefore also be referred to as a "high temperature zone" or "high temperature region". The second temperature zone $TZ_2$ may comprise a lower mean or average temperature than the first and third temperature zones $TZ_1$, $TZ_3$. The second temperature zone $TZ_2$ may therefore also be referred to as a "low temperature zone" or "low temperature region".

For example, a mean temperature in the first temperature zone $TZ_1$ may be higher than a mean temperature in the third temperature zone $TZ_3$, and the mean temperature in the third temperature zone $TZ_3$ may be higher than a mean temperature in the second temperature zone $TZ_2$. Accordingly, the third temperature zone $TZ_3$ may be a transitional zone between the first and second temperature zones $TZ_1$, $TZ_2$.

As mentioned above, the areas $A_1$, $A_2$ of the thermal emitter 16 and/or the heating structure 12, respectively, may be located at different temperature zones $TZ_1$, $TZ_2$, $TZ_3$. For example, the heating element 13 may be arranged in a first area $A_1$, wherein the first area $A_1$ may be located in the first temperature zone $TZ_1$ which may be a "high temperature zone". Additionally or alternatively, the gas adsorbing layer 15 may be arranged in a second area $A_2$, wherein the second area $A_2$ may be located in the second temperature zone $TZ_2$ which may be a "low temperature zone".

Figure 3A:
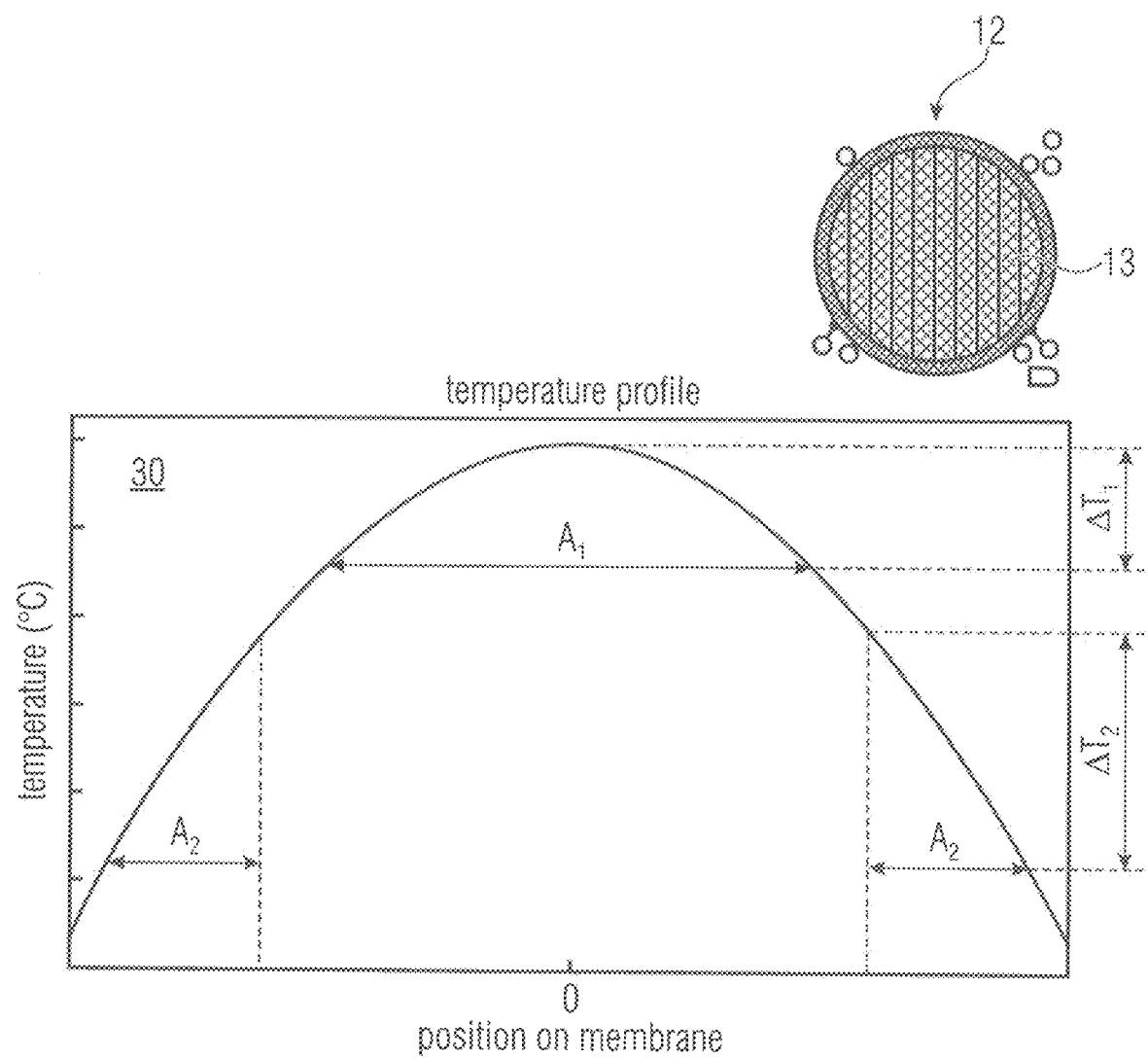
FIG. 3A shows an exemplary temperature profile of a thermal emitter to be used in a MEMS gas sensor according to an embodiment.
Figure 3B:
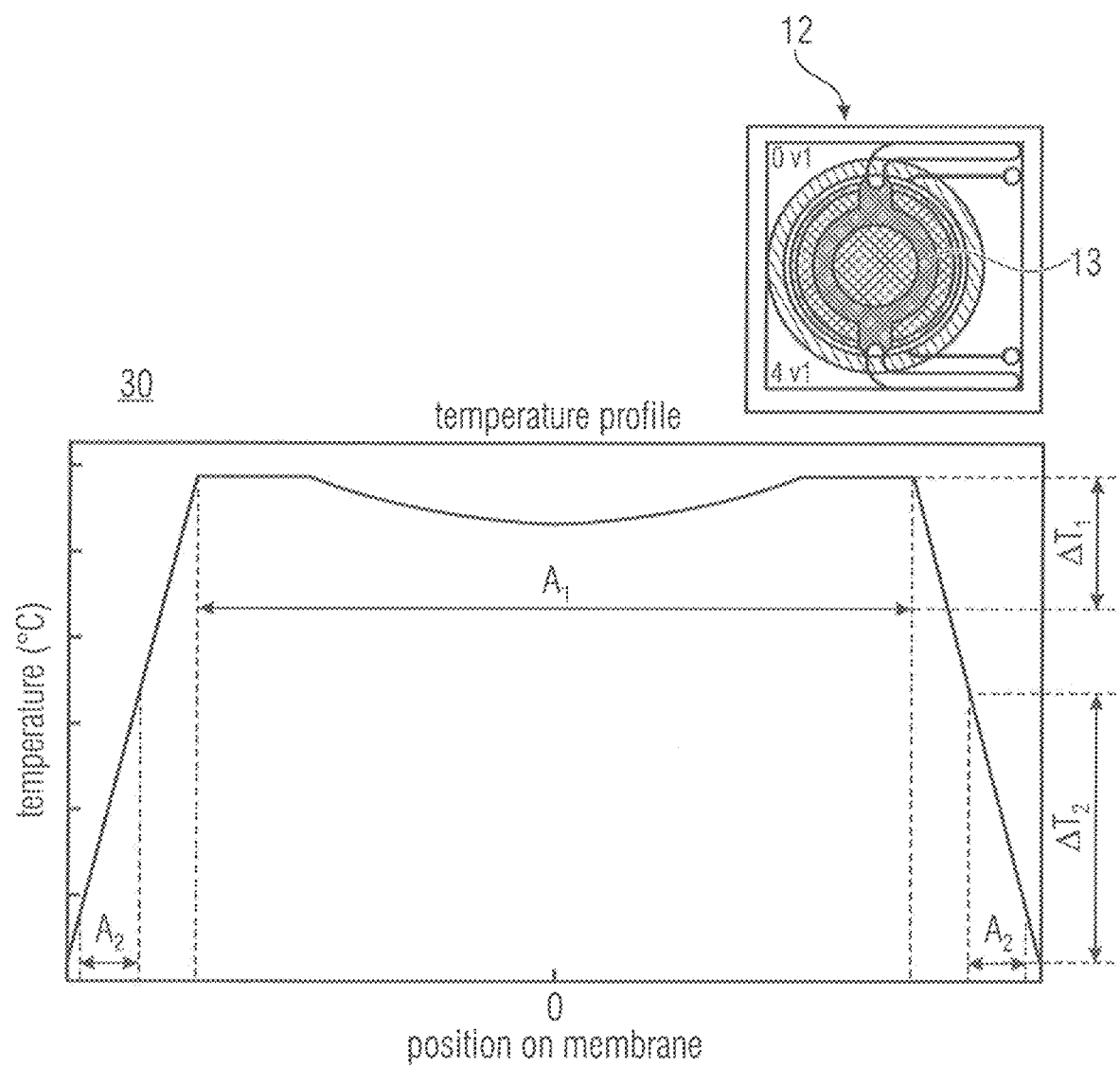
FIG. 3B shows an exemplary temperature profile of a thermal emitter to be used in a MEMS gas sensor according to an embodiment.

FIGS. 3A and 3B show some further exemplary and non-limiting temperature profiles 30 of other exemplary thermal emitters 16.

FIG. 3A shows a temperature profile stemming from a meander structured heating element 13 supported by a heating structure 12. The highest temperature may be reached at the center portion (at position 0 on the x-axis) of the heating structure 12 and heat may slowly decrease towards the peripheral portions of the heating structure 12, i.e. with increasing lateral distance from the center portion. This temperature profile 30 may accordingly indicate the above described first portions $A_1$ comprising a temperature inside an operating temperature range $\Delta T_1$ of the photoacoustic sensor 10 as well as the above described second portions $A_2$ comprising a temperature inside an operating temperature range $\Delta T_2$ of the chemical sensor 14.

FIG. 3B shows a temperature profile stemming from a ring-shaped heating element 13, similar to the one previously discussed with reference to FIG. 2A. The highest temperature may be reached at the ring portion of the heating element 13 while the temperature may slightly decrease towards the center portion of the heating structure 12, i.e. inside the ring-shaped heating element 13. Furthermore, temperature may rapidly drop with decreasing lateral distance from the ring-shaped heating element 13 towards the peripheral portions of the heating structure 12. This temperature profile 30 may also indicate the above described first portion $A_1$ comprising a temperature inside an operating temperature range $\Delta T_1$ of the photoacoustic sensor 10 as well as the above described second portion $A_2$ comprising a temperature inside an operating temperature range $\Delta T_2$ of the chemical sensor 14.

Figure 4A:
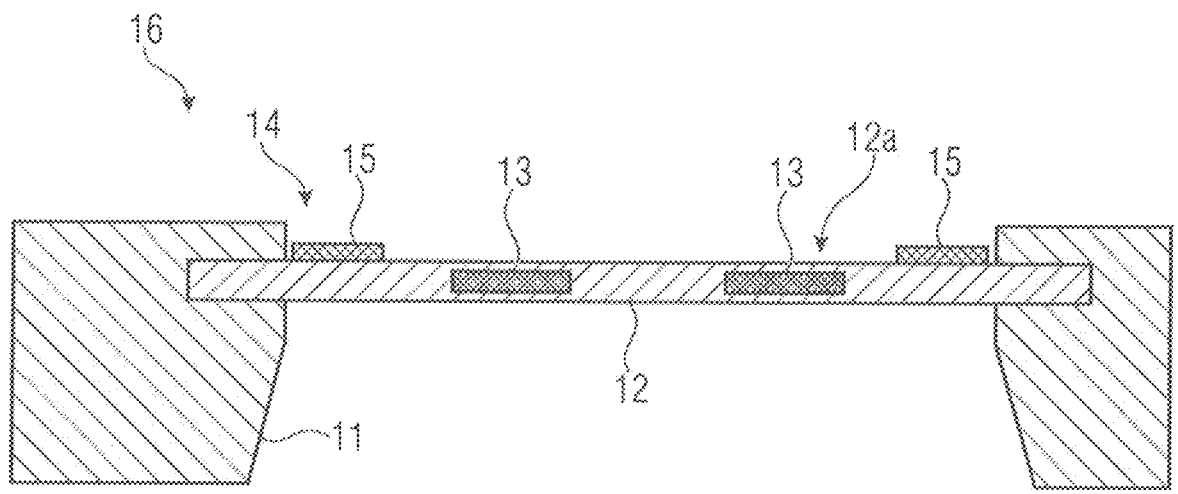
FIG. 4A shows a schematic cross-sectional view of a thermal emitter to be used in a MEMS gas sensor according to an embodiment.
Figure 4B:
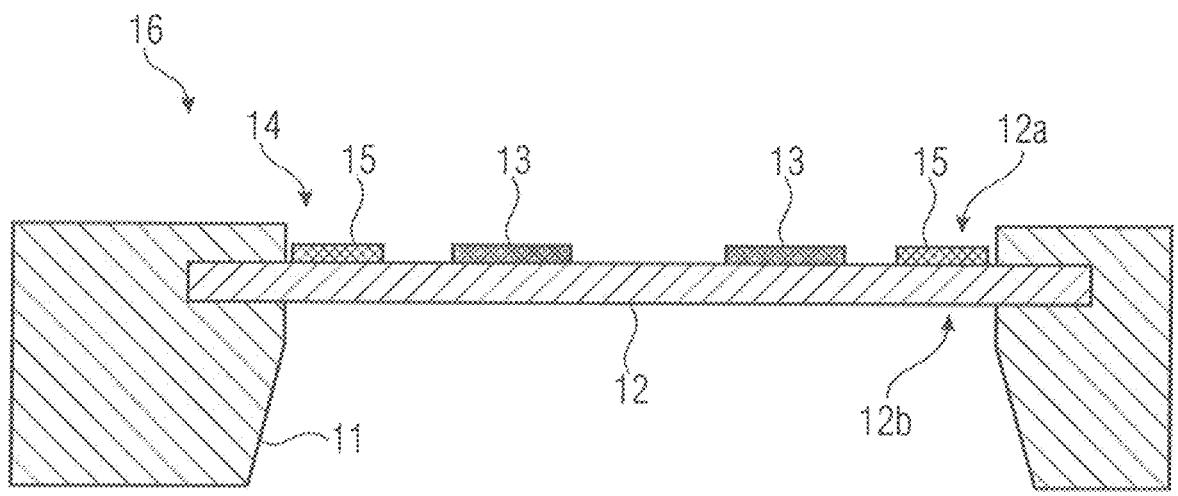
FIG. 4B shows a schematic cross-sectional view of a thermal emitter to be used in a MEMS gas sensor according to an embodiment.

FIGS. 4A and 4B show a further exemplary embodiment of a thermal emitter 16 that may be used in a MEMS gas sensor 100 according to the herein described concept. FIG. 4A shows a schematic sectional side view of a thermal emitter 16, and FIG. 4B shows a schematic top view of said thermal emitter 16.

The thermal emitter 16 comprises a semiconductor substrate 11 and a heating structure 12, e.g. a membrane, being supported by the semiconductor substrate 11. The heating structure 12 may comprise a heating element 13. The heating element 13 may, for instance, be embedded in the heating structure 12.

On one side 12a of the heating structure 12, a chemical sensor 14 may be arranged, the chemical sensor 14 being thermally coupled to the heating element 13. For example, the heating element 13 may produce heat that may be conducted through the heating structure 12 to the adsorbing layer 15. The adsorbing layer 15 may, for instance, comprise graphene which may be precipitated onto the heating structure 12.

Accordingly, the chemical sensor 14, and in particular the gas adsorbing layer 15, may be thermally coupled to at least one of the heating structure 12 and the heating element 13.

According to some embodiments, the chemical sensor 14, and in particular the gas adsorbing layer 15, may be disposed directly on a top or a bottom surface 12a, 12b of the heating structure 12. Thus, the chemical sensor 14, and in particular the gas adsorbing layer 15, may be thermally coupled to the heating element 13 directly through the heating structure 12, i.e. by a direct thermal coupling.

FIG. 4B shows a further example of a thermal emitter 16 that may be used in a MEMS gas sensor 100 according to the herein described concept. A difference to the above discussed embodiment is that the heating element 13 may be supported by the heating structure 12. For example, the heating element 13 may be arranged at at least one of the above mentioned first and second surfaces or sides 12a, 12b of the heating structure 12. For example, the heating element 13 may be deposited onto the heating structure 12. For example, a first layer of silicon nitride may be deposited and then a layer of polysilicon may be deposited. Then, the polysilicon may be doped as will be explained in more detail below with reference to FIG. 6, in order to provide the thermal heating element 13. Then, the (doped) polysilicon may be at least partially structured, e.g. by etching, so that portions of the (doped) polysilicon may be removed and a structured heating element 13 may remain.

At least one of the heating structure 12 and the heating element 13 may be disc-shaped. A disc may be circular or angular, wherein the width of a disc may be smaller than its dimensions in its lateral extension direction.

Figure 5C:
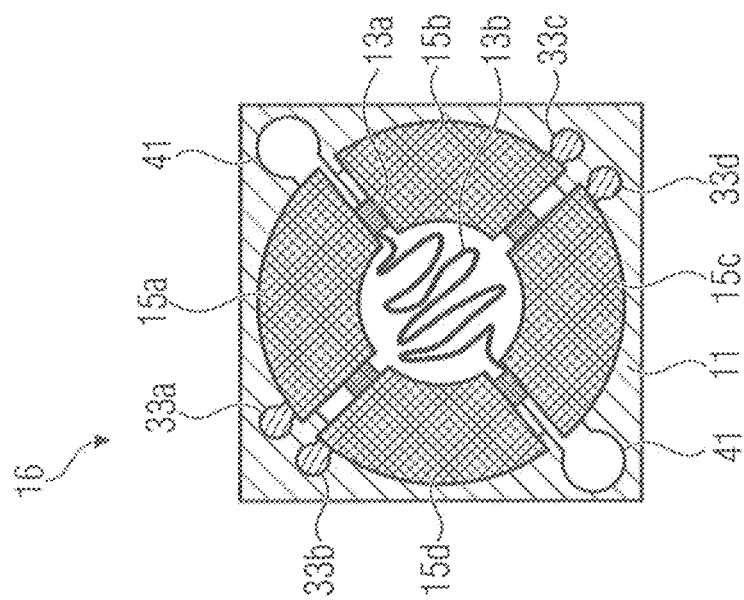
FIGS. 5A-5E show schematic top views of thermal emitters to be used in a MEMS gas sensor according to embodiments.
Figure 5B:
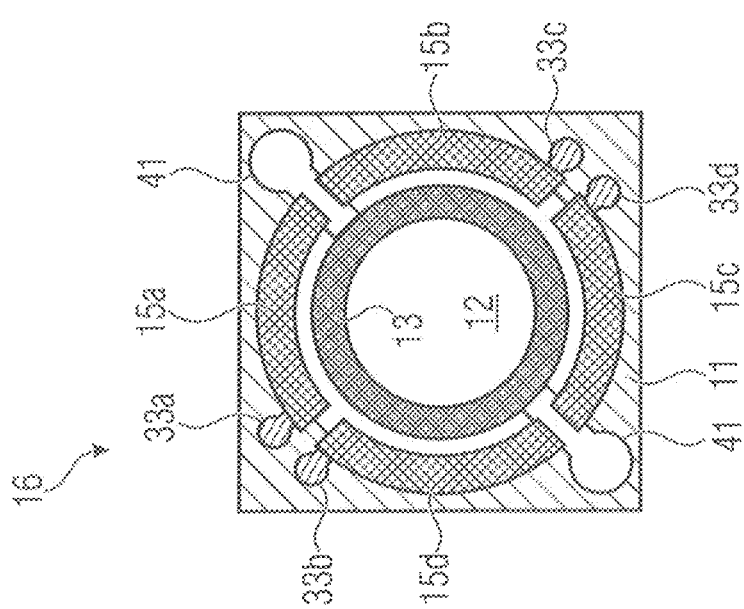
Figure 5A:
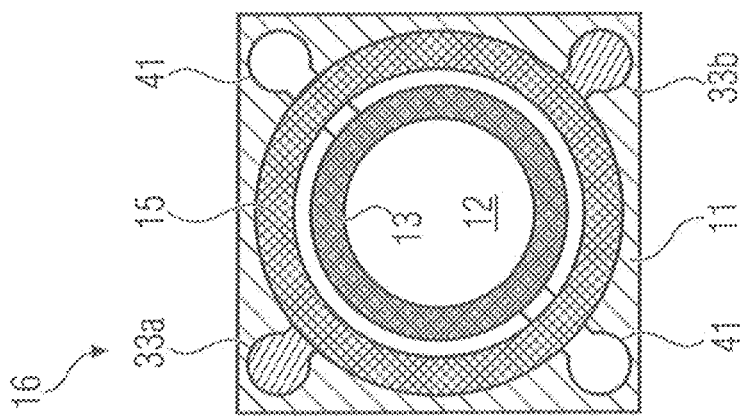
Figure 5D:
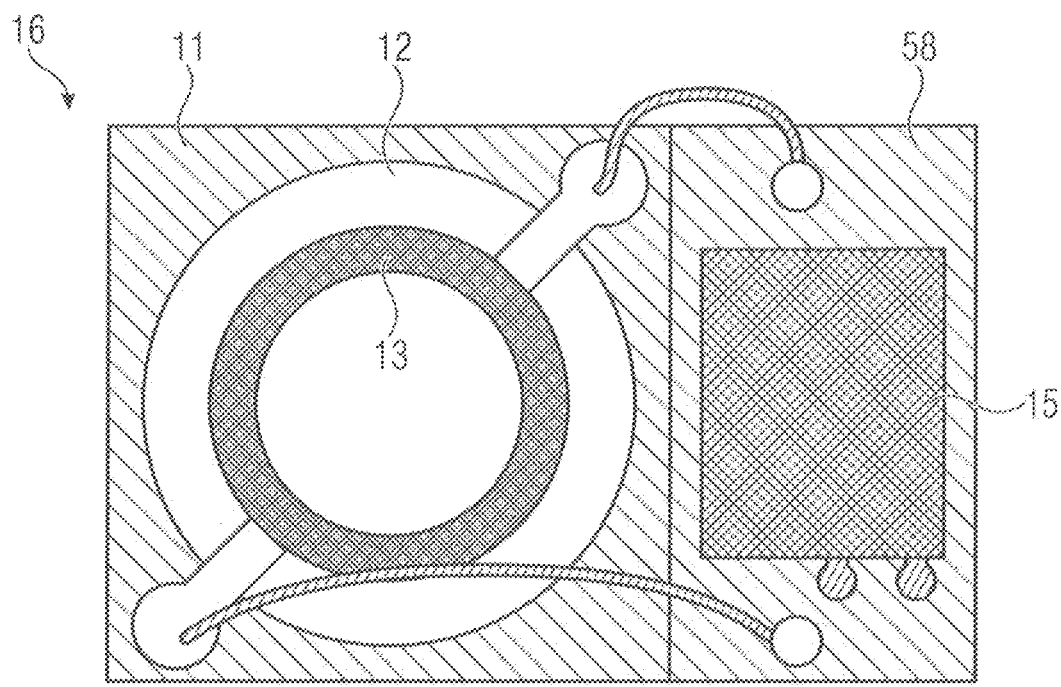
Figure 5E:
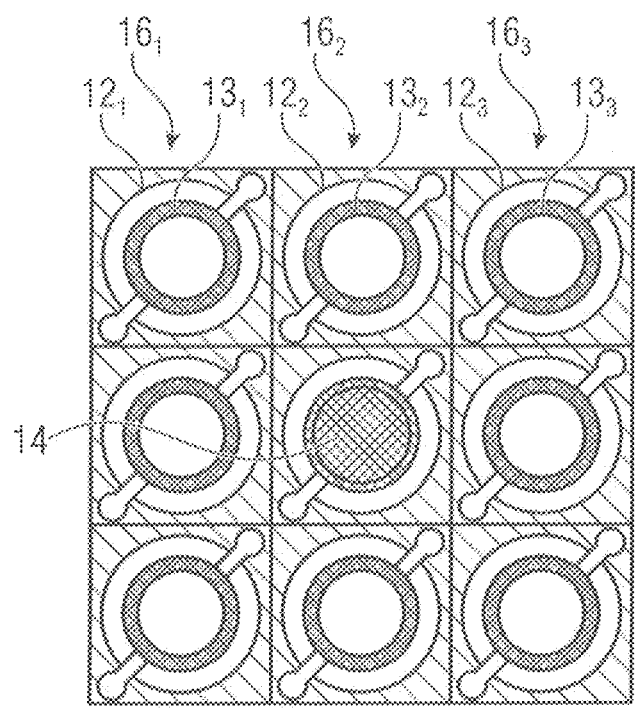
Figure 5F:
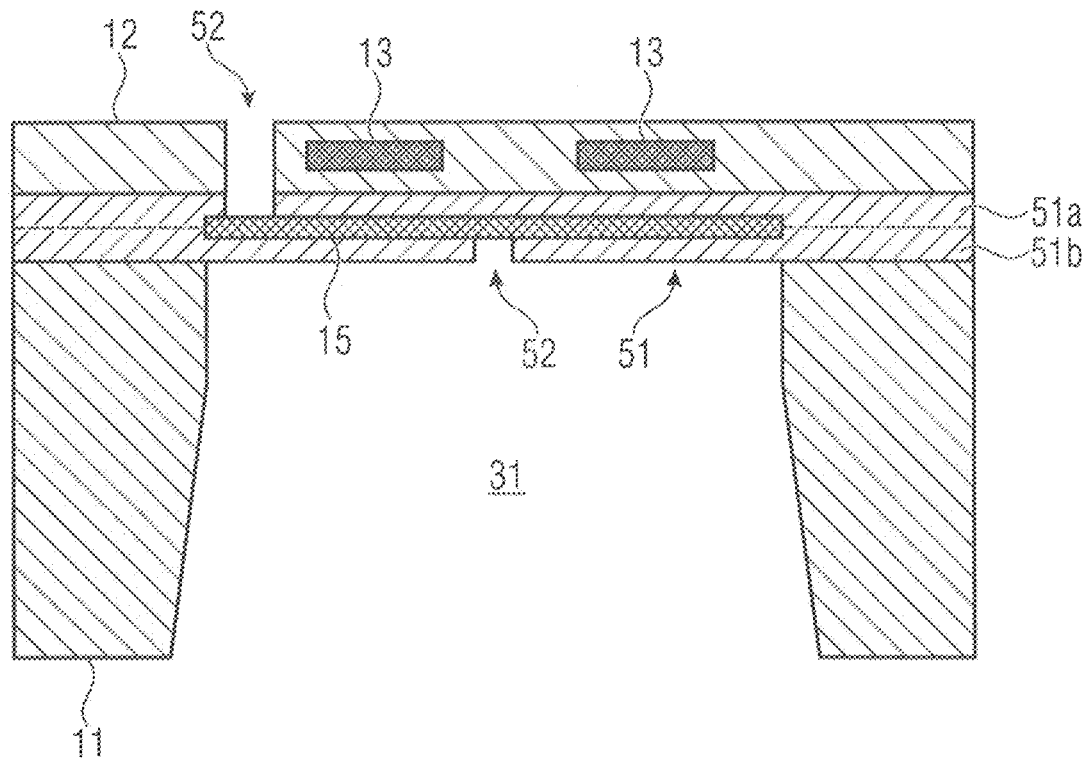
FIG. 5F shows a schematic cross-sectional view of a thermal emitter to be used in a MEMS gas sensor according to an embodiment.

FIGS. 5A, to 5F show some further non-limiting examples of thermal emitters 16 to be used in a MEMS gas sensor 100 according to the herein described concept.

As can be seen, at least one of the heating element 13 and the gas adsorbing layer 15 may be loop-shaped. In some examples (FIGS. 5A, 5B) the footprint of the gas adsorbing layer 15 may laterally surround the footprint of the heating element 13. In other words, the heating element 13 may be arranged further inside or nearer at a center portion of the heating structure 12 than the gas adsorbing layer 15. When viewed in a projection perpendicular to the heating structure 12, the heating element 13 may be arranged inside the gas adsorbing layer 15 and/or the gas adsorbing layer 15 may laterally surround, at least partially, the heating element 13. The heating element 13 and the gas adsorbing layer 15 may be laterally spaced apart from another, when viewed in a projection perpendicular to the heating structure 12, as shown in FIGS. 5A and 5B. Alternatively, as shown in FIG. 5C, the heating element 13 and the gas adsorbing layer 15 may at least partially overlap each other, when viewed in a projection perpendicular to the heating structure 12.

In some further examples, as shown in FIGS. 5B and 5C, the gas adsorbing layer 15 may be segmented into at least two segments 15a, 15b, 15c, 15d, wherein each segment 15a, 15b, 15c, 15d may be configured to be sensitive to a different target gas. Each segment 15a, 15b, 15c, 15d may comprise one or more signal connectors 33a, 33b, 33c, 33d. The signal connectors 33a, 33b, 33c, 33d may be connected to a controller 21, for example, for transmitting a signal created by the chemical sensor 14 to the controller 21 for detecting a target gas based on said transmitted signal. Furthermore, electrical contacts 41 may be provided for electrically contacting and powering the heating element 13.

FIG. 5C shows a further example in which the heating element 13 may comprise two heating members 13a, 13b. The first heating member 13a may be loop-shaped. The first and second heating members 13a, 13b may be arranged in the same plane, i.e. they may be coplanar. The second heating member 13b may be arranged inside the loop-shaped first heating member 13a. Additionally or alternatively, the second heating member 13b may be arranged inside the (segmented) gas adsorbing layer 15, when viewed in a projection perpendicular to the heating structure 12.

According to some examples, the first heating member 13a may be configured to emit heat at a different temperature than the second heating member 13b for creating a predetermined temperature profile 30. For example, one of the first and second heating members 13a, 13b may be configured to emit heat at a temperature inside the operating temperature range $\Delta T_1$ of the photoacoustic sensor 10, and the other one of the first and second heating members 13a, 13b may be configured to emit heat at a temperature inside the operating temperature range $\Delta T_2$ of the chemical sensor 14. Additionally or alternatively, powering only one of the first and second heating members 13a, 13b may cause a temperature inside the operating temperature range $\Delta T_2$ of the chemical sensor 14, while powering both the first and second heating members 13a, 13b may cause a temperature inside the operating temperature range $\Delta T_1$ of the photoacoustic sensor 10.

When viewed in a projection perpendicular to the heating structure 12, the (segmented) gas adsorbing layer 15 may laterally surround one of the first and second heating members 13a, 13b, and the (segmented) gas adsorbing layer 15 may at least partially cover the other one of the first and second heating members 13a, 13b. In this non-limiting example shown in FIG. 5C, the (segmented) gas adsorbing layer 15 may laterally surround the second heating member 13b, and the (segmented) gas adsorbing layer 15 may at least partially cover the first heating member 13a. However, it may also be possible that the (segmented) gas adsorbing layer 15 may laterally surround both the first and second heating members 13a, 13b or neither of them.

FIG. 5D shows a further example of a thermal emitter 16 to be used in a MEMS gas sensor 100 according to the herein described principle. The thermal emitter 16 may comprise one of the several previously discussed heating elements 13 being supported by the heating structure 12. A chemical gas sensor 14 comprising the previously discussed gas adsorbing layer 15 may be arranged next to the thermal emitter 16. The gas sensor 14, and in particular the gas adsorbing layer 15, may be arranged on a separate discrete (electrical) component 58, such as on a MOSFET as a switch, or on an ASIC as a circuit, for example. Said separate discrete component 58 may heat up to a temperature inside a temperature range for operating the chemical sensor 14.

FIG. 5E shows an example of a matrix arrangement of a plurality of thermal emitters 161, 162, 163, . . . , 16n surrounding a chemical gas sensor 14. Each of the thermal emitters 161, 162, 163, . . . , 16n may comprise a previously discussed heating element 131, 132, 133, . . . , 13n each being supported by a previously discussed heating structure 121, 122, 123, . . . , 12n.

FIG. 5F shows a further example of a thermal emitter 16 to be used in a MEMS gas sensor 100 according to the herein described concept. In this example, the heating structure 12 may comprise a first structural member 12a, e.g. a first membrane, and a second structural member 12b, e.g. a second membrane. The first structural member 12a may comprise a heating element 13 that is embedded in the first structural member 12a, as discussed above. The chemical gas sensor 14 may comprise a gas adsorbing layer 15 being embedded in the second structural member 12b. The second structural member 12b may be in direct contact with the first structural member 12a. The second structural member 12b may be thermally coupled with the first structural member 12a. The second structural member 12b may be thermally coupled with the semiconductor substrate 11. The second structural member 12b may be arranged (when viewed in a projection perpendicular to the heating structure 12) above or below the first structural member 12a. At least one of the first and second structural member 12a, 12b may be arranged inside an opening 31 formed in the semiconductor substrate 11.

The above mentioned structural members 12a, 12b are only non-limiting examples. In more general terms, the gas adsorbing layer 15 may be embedded in at least one dielectric material 51. The dielectric material 51 may comprise a first layer 51a of dielectric material and a second layer 51b of dielectric material. The gas adsorbing layer 15 may be arranged between the first layer 51a of dielectric material and the second layer 52b of dielectric material. As can be seen in the non-limiting example of FIG. 5F, the gas adsorbing layer 15 may be disposed underneath the heating structure 12.

According to a further example, at least one opening 52 may be provided in the at least one dielectric material 51, the opening 52 extending between the gas adsorbing layer 15 and an environment for allowing gas to flow from the environment to the gas adsorbing layer 15. Additionally or alternatively, the dielectric material 51 could be porous for allowing a gas exchange towards the gas adsorbing layer 15.

Instead of being embedded in the dielectric material 51, as shown in FIG. 5F, the gas adsorbing layer 15 may be arranged at or on the dielectric material 51, similar to the heating element 13 as previously explained with reference to FIGS. 4A and 4B.

Figure 6:
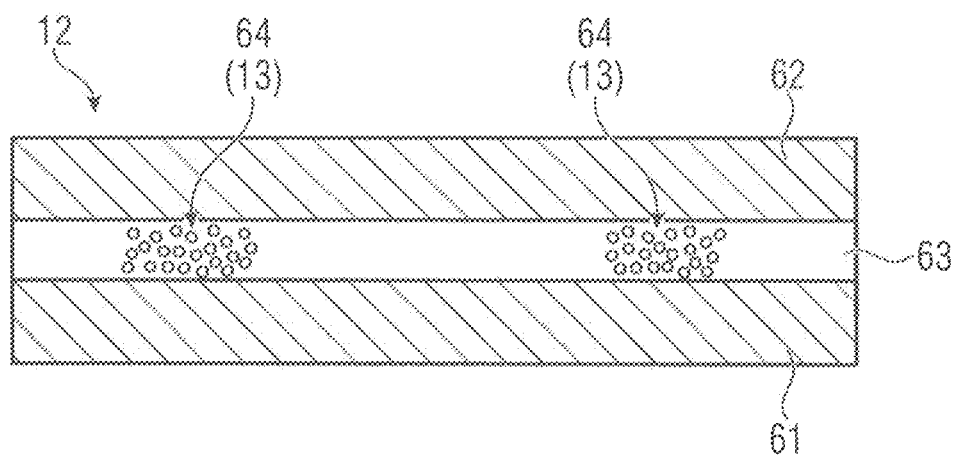
FIG. 6 shows a schematic cross-sectional view of a heating structure to be used in a MEMS gas sensor according to an embodiment.

FIG. 6 shows an example of a heating structure 12 that may be used in thermal emitter 16 according to the herein described principle. For example, the heating structure 12 may comprise a first layer 61 comprising an electrical isolating material such as silicon nitride, and a second layer 62 comprising an isolating material such as silicon nitride. A third layer 63 may comprise the heating element 13 and may be arranged between the first and second layers 61, 62. The third layer 63 may comprise a semiconductor material such as polysilicon. The third layer 63 may comprise doped regions 64 providing structures of higher electrical resistance compared to the rest of the third layer 63. These doped regions 64 in the third layer 63 may form the heating element 13. The first layer 61, second layer 62 and third layer 63 may be integral parts of the heating structure 12. Accordingly, the heating element 13 of this example may be embedded in the heating structure 12.

Additionally or alternatively, the heating element 13 may be arranged on the outside of one of the first and second layers 61, 62, i.e. on the outer periphery of the heating structure 12, rather than being embedded in the heating structure 12. Further additionally or alternatively, the heating element 13 may be a discrete electrical component (e.g., a wire) being arranged between the first and second layer 61, 62 or on the outer periphery of the heating structure 12.

In the following, the principle described herein shall briefly be summarized in other words:

Disclosed is a membrane 12, multi-membrane 12a, 12b or simply heating structure with a defined temperature profile. The "hot" structure or hot part may emit IR light for the physical gas-sensor. The "cold" structure or cold part may be configured to recover/refresh/reset the chemical gas-sensor 14.

Alternatively to black body radiators, electrical power losses can be used to heat up these chemical structures (e.g., in LED technology). The previously unused "cold" non IR emitting area on the IR heater may be used for sensing multi-gas with a gas adsorbing layer 15 comprising functionalized material e.g. MOX, Graphene, . . . .

The above mentioned "hot" structures may feature a temperature range of 450° C. to 900° C. or higher (physical sensing range). The above mentioned "cold" structures may feature a temperature range of 100° C. to 300° C. or lower (chemical sensing range).

The MEMS gas sensor 100 may be a sub part (component) of a bigger system, for example of a Photo Acoustic Spectrometer (PAS sensor) or of a non-dispersive infrared (NDIR) sensor in which the MEMS gas sensor 100 may be used as an infrared emitter. At the same time it may be configured to sense directly the gas concentrations from the environment chemically by the gas adsorbing layer 15. However, the MEMS gas sensor 100 could also be a discrete or separate product. The MEMS gas sensor 100 may, for instance, be used as a standalone multi-gas sensing cell.

The basic principle described herein provides a thermal network between solid membranes including heating structures (sources of heat) and fluid (mostly air, special gas) couplings in between these membranes to conduct and control the temperatures from one membrane to another and achieve a requested temperature profile or temperature pattern or temperature or optical pattern at the top or bottom membrane. The fluid solid interaction for thermics in this sense increases the optical response time by minimizing the thermal capacity.

With the MEMS gas sensor 100 according to this principle, advantages of physical and chemical gas sensors can be combined in on single device. Furthermore, a smaller form factor and customer specific functionalization for chemical sensors, as well as a less complex overall system may be realizable compared to current VOC/$CO_2$ sensors.

According to some embodiments (e.g., FIGS. 5A, 5B), the heating element 13 may be directly on the heating structure 12, surrounded by a possibly segmented chemical functionalized structure 15.

According to some embodiments (e.g., FIG. 5B), a segmented functionalized layer 15 for multi-gas sensing may be provided.

According to some embodiments (e.g., FIG. 5C), a temperature profile with two or more areas may be created by using two or more heating members 13a, 13b.

According to some embodiments (e.g., FIG. 5D), a heating element 13 may be combined with e.g., a MOSFET as switch, where the switch heats up and may be covered with the chemical structure 15.

According to some embodiments (e.g., FIG. 5E), a matrix arrangement of two or more MEMS gas sensors 100 may be provided. Each MEMS sensor 100 may comprise different thicknesses of their heating structure 12 (slower heating, higher thermal mass lead).

According to an aspect, a MEMS gas sensor is provided, the MEMS gas sensor comprising a photoacoustic sensor comprising a thermal emitter and an acoustic transducer, the thermal emitter and the acoustic transducer being arranged inside a mutual measurement cavity, wherein the thermal emitter comprises a semiconductor substrate and a heating structure being supported by the semiconductor substrate, the heating structure including a heating element, and a chemical sensor thermally coupled to the heating element, the chemical sensor including a gas adsorbing layer.

According to a further aspect, the thermal emitter is configured to emit infrared radiation of a first temperature range for operating the photoacoustic sensor and to emit heat of a second temperature range for operating the chemical sensor.

According to a further aspect, the first temperature range $\Delta T_1$ is between 450° C. and more, or between 450° C. and 900° C., and/or the second temperature range $\Delta T_2$ is between 350° C. and less, or between 350° C. and 100° C.

According to a further aspect, the thermal emitter comprises a predetermined temperature profile according to which the heating element is configured to heat a first portion of the thermal emitter to a first temperature and to heat a second portion of the thermal emitter to a second temperature being lower than the first temperature, wherein the adsorbing layer is arranged at the second portion of the thermal emitter.

According to a further aspect, the heating element is configured to heat the first portion of the thermal emitter to the first temperature and to heat the second portion of the thermal emitter to the second temperature during the same activation time.

According to a further aspect, the thermal emitter comprises a predetermined temperature profile according to which the thermal emitter comprises at least three different temperature zones, wherein temperature in the first and second temperature zones varies less than temperature in the third temperature zone.

According to a further aspect, a mean temperature in the third temperature zone is higher than a mean temperature in the second temperature zone and lower than a mean temperature in the first temperature zone.

According to a further aspect, the heating element is arranged at the first temperature zone and the gas adsorbing layer is arranged at the second temperature zone or at the third temperature zone.

According to a further aspect, the gas adsorbing layer is disposed directly on a top or a bottom surface of the heating structure.

According to a further aspect, the heating structure has a central portion and a peripheral portion, the gas adsorbing layer being disposed over or under the heating structure at the peripheral portion.

According to a further aspect, the heating structure is disc-shaped.

According to a further aspect, at least one of the heating element and the gas adsorbing layer is loop-shaped.

According to a further aspect, in a projection perpendicular to the heating structure, the gas adsorbing layer at least partially surrounds the heating element.

According to a further aspect, in a projection perpendicular to the heating structure, the heating element and the gas adsorbing layer at least partially overlap.

According to a further aspect, the gas adsorbing layer is segmented into at least two segments, wherein each segment is configured to be sensitive to a different target gas.

According to a further aspect, the heating element comprises a first heating member and a second heating member, the first heating member being configured to emit heat at a different temperature than the second heating member for creating a predetermined temperature profile.

According to a further aspect, in a projection perpendicular to the heating structure, the gas adsorbing layer laterally surrounds one of the first and second heating members and at least partially covers the other one of the first and second heating members.

According to a further aspect, the gas adsorbing layer is arranged on the semiconductor substrate and/or on the heating structure.

According to a further aspect, the gas adsorbing layer is disposed underneath the heating structure.

According to a further aspect, the gas adsorbing layer is embedded in at least one dielectric material.

According to a further aspect, the at least one dielectric material comprises a first layer of dielectric material and a second layer of dielectric material, and wherein the gas adsorbing layer is arranged between the first layer of dielectric material and the second layer of dielectric material.

According to a further aspect, at least one opening is provided in the at least one dielectric material, the opening extending between the gas adsorbing layer and an environment for allowing gas to flow from the environment to the gas adsorbing layer.

According to a further aspect, the heating element is embedded in the heating structure.

According to a further aspect, the heating structure includes a first layer of dielectric material, the heating element over the first layer of dielectric material, and a second layer of dielectric material over the heating element.

According to a further aspect, the heating element includes a doped polysilicon.

According to a further aspect, the doped polysilicon includes a phosphorous doped polysilicon.

According to a further aspect, the gas adsorbing layer includes graphene.

According to a further aspect, the thermal emitter comprises a filter structure being configured to selectively transmit emitted thermal radiation in a predetermined wavelength.

According to a further aspect, a thermal emitter is provided, the thermal emitter comprising a semiconductor substrate and a heating structure being supported by the semiconductor substrate, the heating structure including a heating element supported by the heating structure, and a chemical sensor thermally coupled to the heating element, the chemical sensor including a gas adsorbing layer.

In the following, some further embodiments of the present disclosure may be described which may all be combinable with the other aspects and embodiments as disclosed and discussed herein.

According to a first embodiment, a MEMS gas sensor may be provided, the MEMS gas sensor comprising:

a substrate comprising a membrane structure, the membrane structure comprising a heating structure for providing heat and for emitting infrared radiation, an adsorbing layer for adsorbing molecules of a surrounding gas, wherein the heating structure is configured to heat a first portion of the MEMS gas sensor to a first predetermined temperature and to heat a second portion of the MEMS gas sensor to a second predetermined temperature being lower than the first predetermined temperature, wherein the adsorbing layer is arranged at the second portion of the MEMS gas sensor.

According to a second embodiment being combinable with the first embodiment, the heating structure comprises a predetermined temperature profile, wherein, when the heating structure is in an active state, the heating structure jointly heats the first area of the substrate and the second area of the substrate at the same time.

According to a third embodiment being combinable with the first or the second embodiment, the MEMS gas sensor is configured to sense a first type of gas based on a physical sensing principle by infrared radiation emitted by the heating structure, and wherein the MEMS gas sensor is configured to sense the first type of gas or a second type of gas based on a chemical sensing principle by the adsorbing layer.

According to a fourth embodiment being combinable with one of the first to third embodiments, the MEMS gas sensor is configured to sense the first type of gas based on the physical sensing principle when the heating structure is in an active state in which it heats the first area of the substrate to the first predetermined temperature.

According to a fourth embodiment being combinable with one of the third or fourth embodiment, the MEMS gas sensor is configured to sense one of the first and second type of gas based on the chemical sensing principle when the heating structure is in an inactive state in which it does not heat the second area of the substrate to the second predetermined temperature.

According to a sixth embodiment being combinable with one of the first to fifth embodiments, the second predetermined temperature lies within a temperature range at which molecules being adsorbed by the adsorbing layer are desorbed from the adsorbing layer in order to refresh the adsorbing layer when the heating structure is in an active state.

According to a seventh embodiment being combinable with one of the first to sixth embodiments, the first predetermined temperature is 400° C. or higher or wherein the first predetermined temperature lies within a range between 450° C. and 900° C., and wherein the second predetermined temperature is 350° C. or lower or wherein the second predetermined temperature lies within a range between 100° C. to 300° C.

According to an eighth embodiment being combinable with one of the first to seventh embodiments, the membrane structure comprises a first membrane comprising the heating structure, wherein the first portion of the MEMS gas sensor that is heated to the first temperature comprises the first membrane, and wherein the second portion of the MEMS gas sensor that is heated to the second temperature comprises the substrate.

According to a ninth embodiment being combinable with one of the first to eighth embodiments, the membrane structure comprises a first membrane and a second membrane, wherein the first membrane comprises the heating structure and wherein the second membrane comprises the adsorbing layer.

According to a tenth embodiment being combinable with the ninth embodiment, the first membrane and the second membrane are piled atop each other when viewed in a projection perpendicular to the first and second membranes.

According to an eleventh embodiment being combinable with one of the ninth or tenth embodiments, the first portion of the MEMS gas sensor being heated to the first temperature comprises the first membrane, and the second portion of the MEMS gas sensor being heated to the second temperature comprises the second membrane.

According to a twelfth embodiment being combinable with one of the first to eleventh embodiments, at least one of the heating structure and the adsorbing layer comprises an annular shape.

According to a thirteenth embodiment being combinable with one of the first to twelfth embodiments, the adsorbing layer is segmented into at least two segments, wherein each segment is configured to be sensitive to a different type of gas.

According to a fourteenth embodiment being combinable with one of the first to thirteenth embodiments, the heating structure is arranged closer to a center of the MEMS gas sensor than the adsorbing layer, when viewed in a projection perpendicular to the membrane.

According to a fifteenth embodiment being combinable with one of the first to fourteenth embodiments, the adsorbing layer at least partially surrounds the heating structure, when viewed in a projection perpendicular to the membrane.

According to a sixteenth embodiment being combinable with one of the first to fifteenth embodiments, the heating structure and the adsorbing layer are laterally spaced from one another, when viewed in a projection perpendicular to the membrane.

According to a seventeenth embodiment being combinable with one of the first to sixteenth embodiments, the heating structure and the adsorbing layer at least partially overlap, when viewed in a projection perpendicular to the membrane.

According to an eighteenth embodiment being combinable with one of the first to seventeenth embodiments, the substrate comprises a plurality of membranes, each comprising a heating structure, wherein the plurality of membranes comprising the heating structures laterally surround the adsorbing layer, when viewed in a projection perpendicular to the membrane.

According to a nineteenth embodiment being combinable with the eighteenth embodiment, the membranes comprise different thicknesses.

According to an twentieth embodiment being combinable with one of the first to nineteenth embodiments, the heating structure comprises a first heating structure and a second heating structure, the first heating structure being activatable independent from the second heating structure for creating the predetermined temperature profile.

According to a twenty-first embodiment being combinable with one of the first to nineteenth embodiments, the heating structure is an infrared heater structure comprising at least one of a laser, a light emitting diode and a resistive heater structure.

According to a twenty-second embodiment being combinable with one of the first to twenty-first embodiments, the heating structure and the adsorbing layer are monolithically integrated on the same chip.

According to a twenty-third embodiment being combinable with one of the first to twenty-second embodiments, the MEMS gas sensor is configured to sense at least $CO_2$.

According to a twenty-fourth being combinable with one of the first to twenty-third embodiments, a MEMS gas sensor is provided comprising, inter alia, a semiconductor substrate. The MEMS gas sensor further comprises a heating structure including a doped polysilicon, wherein the heating structure is supported by the semiconductor substrate. The MEMS gas sensor of the second aspect further comprises a gas adsorbing layer being thermally coupled to the heating structure. For example, doped regions in the polysilicon may have a predetermined electrical resistance, which doped regions produce heat when being energized. Accordingly, the doped regions may form the heating structure. Such doped regions may be provided with very high precision, such that a heating structure providing different temperature regions may be created. In other words, different temperature profiles may easily be provided by said heating structure comprising doped polysilicon.

According to a twenty-fifth embodiment, a photoacoustic sensor system is provided, the photoacoustic sensor system comprising a MEMS gas sensor according to one of the preceding embodiments, wherein the heating structure is configured to provide infrared radiation at a wavelength for operating the photoacoustic sensor system.

According to a twenty-sixth embodiment, a non-dispersive infrared sensor system is provided, the non-dispersive infrared sensor system comprising a MEMS gas sensor according to one of the preceding embodiments, wherein the heating structure is configured to provide infrared radiation at a wavelength for operating the non-dispersive infrared sensor system.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While this disclosure has been described with reference to illustrative embodiments, this description is not intended to be construed in a limiting sense. Various modifications and combinations of the illustrative embodiments, as well as other embodiments of this disclosure, will be apparent to persons skilled in the art upon reference to the description. It is therefore intended that the appended claims encompass any such modifications or embodiments.

What is claimed is:

1. A MEMS gas sensor, comprising:
    a photoacoustic sensor comprising a thermal emitter and an acoustic transducer, the thermal emitter and the acoustic transducer being arranged inside a mutual measurement cavity,
    wherein the thermal emitter comprises a semiconductor substrate and a heating structure being supported by the semiconductor substrate, the heating structure including a heating element, and
    a chemical sensor thermally coupled to the heating element, the chemical sensor including a gas adsorbing layer,
    wherein the thermal emitter comprises a predetermined temperature profile according to which the thermal emitter comprises at least three different temperature zones including a first temperature zone, a second temperature zone, and a third temperature zone, and wherein temperature in the first and second temperature zones varies less than temperature in the third temperature zone.

2. The MEMS gas sensor of claim 1, wherein the thermal emitter is configured to emit infrared radiation of a first temperature range for operating the photoacoustic sensor and to emit heat of a second temperature range for operating the chemical sensor.

3. The MEMS gas sensor of claim 2,
    wherein the first temperature range is between 450° C. and 900° C., and/or
    wherein the second temperature range is between 350° C. and 100° C.

4. The MEMS gas sensor of claim 1, wherein a mean temperature in the third temperature zone is higher than a mean temperature in the second temperature zone and lower than a mean temperature in the first temperature zone.

5. The MEMS gas sensor of claim 1, wherein the heating element is arranged at the first temperature zone and the gas adsorbing layer is arranged at the second temperature zone or at the third temperature zone.

6. The MEMS gas sensor of claim 1, wherein the gas adsorbing layer is disposed directly on a top or a bottom surface of the heating structure.

7. The MEMS gas sensor of claim 1, wherein the heating structure has a central portion and a peripheral portion, the gas adsorbing layer being disposed over or under the heating structure at the peripheral portion.

8. The MEMS gas sensor of claim 1, wherein the heating structure is disc-shaped.

9. The MEMS gas sensor of claim 1, wherein at least one of the heating element and the gas adsorbing layer is loop-shaped.

10. The MEMS gas sensor of claim 1, wherein, in a projection perpendicular to the heating structure, the gas adsorbing layer at least partially surrounds the heating element.

11. The MEMS gas sensor of claim 1, wherein, in a projection perpendicular to the heating structure, the heating element and the gas adsorbing layer at least partially overlap.

12. The MEMS gas sensor of claim 1, wherein the gas adsorbing layer is segmented into at least two segments, wherein each segment is configured to be sensitive to a different target gas.

13. The MEMS gas sensor of claim 1, wherein the heating element comprises a first heating member and a second heating member, the first heating member being configured to emit heat at a different temperature than the second heating member for creating the predetermined temperature profile.

14. The MEMS gas sensor of claim 13, wherein, in a projection perpendicular to the heating structure, the gas adsorbing layer laterally surrounds one of the first and second heating members and at least partially covers the other one of the first and second heating members.

15. The MEMS gas sensor of claim 1, wherein the gas adsorbing layer is arranged on the semiconductor substrate and/or on the heating structure.

16. The MEMS gas sensor of claim 1, wherein the gas adsorbing layer is disposed underneath the heating structure.

17. The MEMS gas sensor of claim 1, wherein the gas adsorbing layer is embedded in at least one dielectric material.

18. The MEMS gas sensor of claim 17, wherein the at least one dielectric material comprises a first layer of dielectric material and a second layer of dielectric material, and wherein the gas adsorbing layer is arranged between the first layer of dielectric material and the second layer of dielectric material.

19. The MEMS gas sensor of claim 17, wherein at least one opening is provided in the at least one dielectric material, the opening extending between the gas adsorbing layer and an environment for allowing gas to flow from the environment to the gas adsorbing layer.

20. The MEMS gas sensor of claim 1, wherein the heating element is embedded in the heating structure.

21. The MEMS gas sensor of claim 1, wherein the heating structure includes
    a first layer of dielectric material,
    the heating element over the first layer of dielectric material, and
    a second layer of dielectric material over the heating element.

22. The MEMS gas sensor of claim 1, wherein the heating element includes a doped polysilicon.

23. The MEMS gas sensor of claim 22, wherein the doped polysilicon includes a phosphorous doped polysilicon.

24. The MEMS gas sensor of claim 1, wherein the gas adsorbing layer includes graphene.

25. The MEMS gas sensor of claim 1,
    wherein the thermal emitter comprises a filter structure being configured to selectively transmit emitted thermal radiation in a predetermined wavelength.

26. A thermal emitter comprising:
    a semiconductor substrate and a heating structure being supported by the semiconductor substrate, the heating structure including a heating element supported by the heating structure, and
    a chemical sensor thermally coupled to the heating element, the chemical sensor including a gas adsorbing layer,
    wherein the thermal emitter comprises a predetermined temperature profile according to which the thermal emitter comprises at least three different temperature zones including a first temperature zone, a second temperature zone, and a third temperature zone, and wherein temperature in the first and second temperature zones varies less than temperature in the third temperature zone.

27. A MEMS gas sensor, comprising:
a photoacoustic sensor comprising a thermal emitter and an acoustic transducer, the thermal emitter and the acoustic transducer being arranged inside a mutual measurement cavity,
wherein the thermal emitter comprises a semiconductor substrate and a heating structure being supported by the semiconductor substrate, the heating structure including a heating element, and
a chemical sensor thermally coupled to the heating element, the chemical sensor including a gas adsorbing layer,
wherein the thermal emitter comprises a predetermined temperature profile according to which the heating element is configured to heat a first portion of the thermal emitter to a first temperature and to heat a second portion of the thermal emitter to a second temperature being lower than the first temperature, wherein the adsorbing layer is arranged at the second portion of the thermal emitter, and
wherein the heating element is configured to heat the first portion of the thermal emitter to the first temperature and to heat the second portion of the thermal emitter to the second temperature during the same activation time.

* * * * *